(12) United States Patent
Yoshioka et al.

(10) Patent No.: US 12,404,367 B2
(45) Date of Patent: Sep. 2, 2025

(54) DEGRADABLE MULTI-ARM POLYETHYLENE GLYCOL DERIVATIVE

(71) Applicants: NOF CORPORATION, Tokyo (JP); TOKYO INSTITUTE OF TECHNOLOGY, Tokyo (JP)

(72) Inventors: Hiroki Yoshioka, Kawasaki (JP); Ken Hamura, Kawasaki (JP); Kazuki Osakama, Kawasaki (JP); Nobuhiro Nishiyama, Tokyo (JP)

(73) Assignees: NOF CORPORATION, Tokyo (JP); TOKYO INSTITUTE OF TECHNOLOGY, Tokyo (JP)

( * ) Notice: Subject to any disclaimer, the term of this patent is extended or adjusted under 35 U.S.C. 154(b) by 759 days.

(21) Appl. No.: 17/763,498

(22) PCT Filed: Sep. 25, 2020

(86) PCT No.: PCT/JP2020/036197
§ 371 (c)(1),
(2) Date: Mar. 24, 2022

(87) PCT Pub. No.: WO2021/060441
PCT Pub. Date: Apr. 1, 2021

(65) Prior Publication Data
US 2022/0380533 A1    Dec. 1, 2022

(30) Foreign Application Priority Data

Sep. 26, 2019 (JP) .................. 2019-176230

(51) Int. Cl.
| | |
|---|---|
| *C08G 65/333* | (2006.01) |
| *C07K 5/103* | (2006.01) |
| *C07K 7/06* | (2006.01) |
| *C07K 14/46* | (2006.01) |
| *C08G 83/00* | (2006.01) |

(52) U.S. Cl.
CPC .......... *C08G 65/333* (2013.01); *C07K 5/1008* (2013.01); *C07K 7/06* (2013.01); *C07K 14/46* (2013.01); *C08G 83/003* (2013.01)

(58) Field of Classification Search
None
See application file for complete search history.

(56) References Cited

U.S. PATENT DOCUMENTS

| | | |
|---|---|---|
| 2009/0023859 A1 | 1/2009 | Sakanoue et al. |
| 2010/0010158 A1 | 1/2010 | McManus et al. |
| 2011/0142886 A1 | 6/2011 | Mirosevich et al. |
| 2011/0229528 A1 | 9/2011 | Mirosevich et al. |
| 2018/0214561 A1* | 8/2018 | Weng ............... C08G 65/33324 |

FOREIGN PATENT DOCUMENTS

| | | |
|---|---|---|
| CN | 106421806 A | 2/2017 |
| JP | 2009-527581 A | 7/2009 |
| WO | WO-2005/108463 A2 | 11/2005 |
| WO | WO-2006/088248 A1 | 8/2006 |

OTHER PUBLICATIONS

Dai et al., "Novel Multiarm Polyethylene glycol-dihydroartemisinin conjugates enhancing therapeutic efficacy in non-small-cell lung cancer", Scientific Reports, 4, 5871 (Jul. 29, 2014).

European Medicines Agency, Science Medicines Health, "CHMP Safety Working Party's response to the PDCO regarding the use of PEGylated drug products in the paediatric population", EMA/CHMP/SWP/647258/2012 (Nov. 16, 2012).

Giorgi et al., "Improved bioavailability of inhibitors of Trypanosoma cruzi trans-sialidase: PEGylation of lactose analogs with multiarm polyethyleneglycol", Glycobiology, vol. 22, No. 10, pp. 1363-1373 (2012).

Rudmann et al., "High Molecular Weight Polyethylene Glycol Cellular Distribution and PEG-associated Cytoplasmic Vacuolation is Molecular Weight Dependent and Does Not Require Conjugation to Proteins", Toxicologic Pathology, 41:970-983 (2013).

Veronese et al., "PEG-Doxorubicin Conjugates: Influence of Polymer Structure on Drug Release, in Vitro Cytotoxicity, Biodistribution, and Antitumor Activity", Bioconjugate Chem., 16:775-784 (2005).

Yang et al., "Synthesis and characterization of enzymatically degradable PEG-based peptide-containing hydrogels", Macromol Biosci., 10(4):445-454 (2010).

(Continued)

*Primary Examiner* — Eli D. Strah
(74) *Attorney, Agent, or Firm* — MARSHALL, GERSTEIN & BORUN LLP

(57) ABSTRACT

A multi-arm, degradable polyethylene glycol derivative with a high molecular weight that does not cause vacuolation of cells is provided. A degradable polyethylene glycol derivative represented by the following formula (1):

$$[X^1-L^1-(CH_2CH_2O)_{n1}-L^3\underset{a1}{\overset{}{\longrightarrow}}W^1-L^5-Q-L^6- \\ -W^2-L^4-(OCH_2CH_2)_{n2}-L^2-X^2]_{a2} \tag{1}$$

wherein n1 and n2 are each independently 45-950, $W^1$ and $W^2$ are each independently an oligopeptide of 2-47 residues, a1 and a2 are each independently 1-8, Q is a hydrocarbon chain having 2-12 carbon atoms and optionally containing an oxygen atom and/or a nitrogen atom, $X^1$ and $X^2$ are each independently a functional group capable of reacting with a bio-related substance, and $L^1$, $L^2$, $L^3$, $L^4$, $L^5$ and $L^6$ are each independently a divalent spacer.

15 Claims, No Drawings
Specification includes a Sequence Listing.

(56) References Cited

OTHER PUBLICATIONS

International Search Report for PCT/JP2020/036197 dated Dec. 15, 2020.

* cited by examiner

DEGRADABLE MULTI-ARM POLYETHYLENE GLYCOL DERIVATIVE

CROSS REFERENCE TO RELATED APPLICATIONS

This application is a U.S. National Stage of International Application No. PCT/JP2020/036197, filed Sep. 25, 2020, which claims the benefit of Japanese Patent Application No. 2019-176230, filed Sep. 26, 2019, the entire contents of each of which are fully incorporated herein by reference.

INCORPORATION BY REFERENCE OF MATERIAL SUBMITTED ELECTRONICALLY

A Sequence Listing, which is a part of the present disclosure, is submitted concurrently with the specification as a text file. The name of the text file containing the Sequence Listing is "57781_Seqlisting.txt." The Sequence Listing was created on Mar. 22, 2022, and is 679 Bytes in size. The subject matter of the Sequence Listing is incorporated by reference herein in its entirety.

TECHNICAL FIELD

The present invention relates to a multi-arm degradable polyethylene glycol derivative that is degraded in the cells and used for modifying bio-related substances.

BACKGROUND ART

Pharmaceutical products that use bio-related substances such as hormone, cytokine, antibody, and enzyme are generally rapidly discharged from the body after administration to the body due to glomerular filtration in the kidney and uptake by macrophages in the liver and spleen. Therefore, the half-life in blood is short, and it is often difficult to obtain a sufficient pharmacological effect. To solve this problem, attempts have been made to chemically modify bio-related substances with sugar chain, hydrophilic polymers such as polyethylene glycol, albumin, and the like. As a result, it becomes possible to prolong the blood half-life of bio-related substances by increasing the molecular weight, forming a hydration layer, and the like. In addition, it is also well known that modification with polyethylene glycol provides effects such as reduction of toxicity and antigenicity of bio-related substances, and improvement of solubility of hardly water-soluble drugs.

The bio-related substances modified with polyethylene glycol are covered with a hydration layer formed by an ether bond of polyethylene glycol and a hydrogen bond with water molecule, has an increased molecular size, and thus can avoid glomerular filtration in the kidney. Furthermore, it is known that the interaction with opsonin and the cell surface that constitutes each tissue decreases, and the migration to each tissue decreases. Polyethylene glycol is a superior material that extends the blood half-life of bio-related substances, and it has been found as regards the property thereof that a higher effect is obtained when the molecular weight is higher. Many studies have been made on bio-related substances modified with high-molecular-weight polyethylene glycol with a molecular weight of not less than 40,000, and the results show that the half-life in blood thereof can be significantly extended.

Polyethylene glycol is regarded as the optimum standard among the modifying agents used for improving the property of bio-related substances. At present, a plurality of polyethylene glycol-modified formulations is placed on the market and used in medical sites. On the other hand the European Medicines Agency (EMA) reported in 2012 that administration of a bio-related substance modified with high-molecular-weight polyethylene glycol with a molecular weight of 40,000 or more to an animal for a long time at a certain dose or above led to a phenomenon of the generation of vacuoles in the cells of a part of the tissues (non-patent document 1). In consideration of the facts that there is no report at present that the vacuole formation itself has an adverse effect on the human body, and the dose used in the above EMA report is extremely high compared to the dose generally applied in medical sites, the safety of therapeutic preparations modified with polyethylene glycol having a molecular weight of 40,000 or more which are currently manufactured and sold does not pose any problem. However, in the treatment of very special diseases (e.g., dwarfism), it may be assumed that a treatment protocol in which a polyethylene glycol-modified preparation is administered to a patient at a high dose for a long period of time will be adopted. Therefore, it is expected that a potential demand exists for the development of a polyethylene glycol-modified preparation that does not cause vacuole formation in cells and can be applied even in such a special situation.

In non-patent document 2, a large excess of polyethylene glycol alone was administered to animals for a long term compared to the dose of general polyethylene glycol-modified preparations. As a result, vacuole was not seen at a molecular weight of 20,000, and the generation of vacuole was confirmed at a molecular weight of 40,000. One of the means to suppress vacuoles is to reduce the molecular weight of polyethylene glycol. However, reducing the molecular weight causes a problem that the half-life in blood of bio-related substances cannot be improved sufficiently.

There are reports relating to the technique for degrading high-molecular-weight polyethylene glycol into low-molecular-weight polyethylene glycol in the body and promoting excretion from the kidney. Patent document 1 describes a polyethylene glycol derivative having a sulfide bond or peptide binding site that is cleaved in vivo. It is described that the polyethylene glycol derivative is degraded in vivo to a molecular weight suitable for excretion from the kidney. However, no specific data relating to the degradation is shown, nor is there any data on enhanced excretion from the kidney. Furthermore, there is no description about the vacuoles in cells.

Patent document 2 describes a polyethylene glycol derivative having an acetal site that can be hydrolyzed under low pH environment in the body. It is described that the polyethylene glycol derivative is degraded in vivo to a molecular weight suitable for excretion from the kidney. However, no specific data on enhanced excretion from the kidney is shown. Furthermore, there is no description about the vacuoles in cells. In addition, the hydrolyzable acetal moiety is known to gradually degrade also in blood, and it is expected that the half-life in blood of modified bio-related substances cannot be improved sufficiently.

On the other hand there are reports on polyethylene glycol derivatives containing degradable oligopeptides introduced thereinto for effective release of drugs, hydrogels that degrade in the body, and the like.

Non-patent document 3 describes a polyethylene glycol derivative having an oligopeptide site that is degraded by enzymes. Here, the oligopeptide was introduced as a linker between an anticancer agent and polyethylene glycol, and it has been reported that the oligopeptide is degraded by the enzyme specifically expressed around the tumor, and the anticancer agent is efficiently released. The purpose is release of an anticancer agent, and the degradability is not imparted to polyethylene glycol for the purpose of suppressing cell vacuoles.

Non-patent document 4 describes hydrogels using cross-linking molecules having an oligopeptide site that is degraded by enzymes and a multi-branched polyethylene glycol derivative. Here, the oligopeptide is used as a cross-linking molecule that connects the multi-branched polyethylene glycol derivative, and can further impart degradability by enzymes to the hydrogel. It aims to prepare a degradable hydrogel, where the degradability is not imparted to polyethylene glycol for the purpose of suppressing cell vacuoles.

Patent document 3 describes a branched polyethylene glycol derivative with oligopeptide as the skeleton. Here, oligopeptide is used as the basic skeleton of polyethylene glycol derivatives and does not impart degradability by enzymes. It is characterized by containing amino acids having an amino group or a carboxyl group in the side chain, such as lysine and aspartic acid, in the oligopeptide, and aims to synthesize a branched polyethylene glycol derivative by utilizing them in the reaction. Patent document 3 is not directed to a polyethylene glycol derivative for the purpose of suppressing cell vacuoles.

Polyethylene glycol derivatives used for modifying bio-related substances include a multi-arm type. As described in Non Patent Literature 5 and Non Patent Literature 6, it is described that plural bio-related substances can be bonded in one molecule of a multi-arm polyethylene glycol derivative, and a multi-arm type significantly improves solubility and prolongs the half-life in blood of bio-related substances. Multi-arm polyethylene glycol derivatives are known to carry many drugs and can increase the activity of the drugs, and therefore, are used for many studies. However, there have been no reports on a multi-arm polyethylene glycol derivative that suppresses cell vacuoles.

As described above, a multifunctional multi-arm high-molecular-weight polyethylene glycol derivative that is stable in blood, improves half-life in blood of the modified bio-related substance, is specifically degraded in cell when taken up by cells, and can suppress generation of vacuoles in cells is demanded.

CITATION LIST

Patent Literature

[PTL 1]
Japanese Translation of PCT Application Publication No. 2009-527581
[PTL 2]
WO2005/108463
[PTL 3]
WO2006/088248

Non Patent Literature

[NPL 1]
EMA/CHMP/SWP/647258/2012
[NPL 2]
Daniel G. Rudmann, et al., Toxicol. Pathol., 41, 970-983 (2013)
[NPL 3]
Francesco M Veronese, et al., Bioconjugate Chem., 16, 775-784(2005)
[NPL 4]
Jiyuan Yang, et al., Marcomol. Biosci., 10(4), 445-454 (2010)
[NPL 5]
Lin Dai, et al., Scientific Reports, 29 July (2014)
[NPL 6]
M. Eugenia Giorgi, et al., Glycobiology, 22(10), 1363-1373 (2012)

SUMMARY OF INVENTION

Technical Problem

The problem of the present invention is to provide a high-molecular-weight multi-arm polyethylene glycol derivative that does not cause vacuolation of cells. More specifically, it is to provide a multi-arm degradable polyethylene glycol derivative that can be effectively used for modifying bio-related substances, is stable in the blood of living organisms, and is degraded in cells, by an industrially producible method.

Solution to Problem

The present inventors have conducted intensive studies in an attempt to solve the aforementioned problems and invented a multi-arm degradable polyethylene glycol derivative having an oligopeptide that degrades in cells.

Accordingly, the present invention provides the following.

[1] A degradable polyethylene glycol derivative represented by the following formula (1):

$$[X^1-L^1+(CH_2CH_2O)_{n1}-L^3]_{a1}-W^1-L^5-Q-L^6-W^2+L^4+(OCH_2CH_2)_{n2}-L^2-X^2]_{a2} \quad \text{formula (1)}$$

wherein n1 and n2 are each independently 45-950, $W^1$ and $W^2$ are each independently an oligopeptide of 2-47 residues, a1 and a2 are each independently 1-8, Q is a hydrocarbon chain having 2-12 carbon atoms and optionally containing an oxygen atom and/or a nitrogen atom, $X^1$ and $X^2$ are each independently a functional group capable of reacting with a bio-related substance, and $L^1, L^2, L^3, L^4, L^5$ and $L^6$ are each independently a divalent spacer.

[2] The degradable polyethylene glycol derivative of [1], wherein the oligopeptide for $W^1$ and $W^2$ is an oligopeptide having glycine as a C-terminal amino acid.

[3] The degradable polyethylene glycol derivative of any one of [1]-[2], wherein the oligopeptide for $W^1$ and $W^2$ is an oligopeptide having at least one hydrophobic neutral amino acid having a hydropathy index of not less than 2.5.

[4] A degradable polyethylene glycol derivative represented by the following formula (2):

$$X^1-L^1-(CH_2CH_2O)_{n3}-L^3-W^3-L^5-Q-L^6-W^4-L^4-(OCH_2CH_2)_{n4}-L^2-X^2 \quad \text{formula (2)}$$

wherein n3 and n4 are each independently 110-950, $W^3$ and $W^4$ are each independently an oligopeptide of 2-5 residues, Q is a hydrocarbon chain having 2-12 carbon atoms and optionally containing an oxygen atom and/or a nitrogen atom, $X^1$ and $X^2$ are each independently a functional group capable of reacting with a bio-related substance, and $L^1, L^2, L^3, L^4, L^5$ and $L^6$ are each independently a divalent spacer.

[5] The degradable polyethylene glycol derivative of [4], wherein the oligopeptide for $W^3$ and $W^4$ is an oligopeptide composed only of a neutral amino acid and having glycine as a C-terminal amino acid.

[6] The degradable polyethylene glycol derivative of any one of [4]-[5], wherein the oligopeptide for $W^3$ and $W^4$ is an oligopeptide having at least one hydrophobic neutral amino acid having a hydropathy index of not less than 2.5.

[7] A degradable polyethylene glycol derivative represented by the following formula (3):

$$[X^1-L^1-(CH_2CH_2O)_{n1}-L^3]_{b1}-W^5-L^5-Q-L^6-W^6-[L^4-(OCH_2CH_2)_{n2}-L^2-X^2]_{b2} \quad \text{formula (3)}$$

wherein n1 and n2 are each independently 45-950, $W^5$ and $W^6$ are each independently an oligopeptide consisting of 5 to 47 residues and having a symmetrical structure centered on glutamic acid, b1 and b2 are each independently 2-8, Q is a hydrocarbon chain having 2-12 carbon atoms and optionally containing an oxygen atom and/or a nitrogen atom, $X^1$ and $X^2$ are each independently a functional group capable of reacting with a bio-related substance, and $L^1, L^2, L^3, L^4, L^5$ and $L^6$ are each independently a divalent spacer.

[8] The degradable polyethylene glycol derivative of [7], wherein the oligopeptide with a symmetrical structure centered on glutamic acid for $W^5$ and $W^6$ is an oligopeptide having a structure of the following v1 or v2 or v3:

$$-Glu\begin{matrix}Z-\\Z-\end{matrix} \quad \text{(v1)}$$

$$-Glu\begin{matrix}Glu\begin{matrix}Z-\\Z-\end{matrix}\\Glu\begin{matrix}Z-\\Z-\end{matrix}\end{matrix} \quad \text{(v2)}$$

-continued $$-Glu\begin{matrix}Glu\begin{matrix}Glu\begin{matrix}Z-\\Z-\end{matrix}\\Glu\begin{matrix}Z-\\Z-\end{matrix}\end{matrix}\\Glu\begin{matrix}Glu\begin{matrix}Z-\\Z-\end{matrix}\\Glu\begin{matrix}Z-\\Z-\end{matrix}\end{matrix}\end{matrix} \quad \text{(v3)}$$

wherein Glu is a glutamic acid residue, and Z is a degradable oligopeptide of 2-5 residues consisting of neutral amino acids excluding cysteine.

[9] The degradable polyethylene glycol derivative of [8], wherein the degradable oligopeptide for Z is an oligopeptide having glycine as a C-terminal amino acid.

[10] The degradable polyethylene glycol derivative of any one of [7] to [9], wherein the degradable oligopeptide for Z is an oligopeptide having at least one hydrophobic neutral amino acid having a hydropathy index of not less than 2.5.

[11] The degradable polyethylene glycol derivative of any one of [1] to [10], wherein the total molecular weight is not less than 20,000.

[12] The degradable polyethylene glycol derivative of any one of [1] to [11], wherein $X^1$ and $X^2$ are each independently selected from the group consisting of an active ester group, an active carbonate group, an aldehyde group, an isocyanate group, an isothiocyanate group, an epoxide group, a maleimide group, a vinylsulfonyl group, an acrylic group, a sulfonyloxy group, a carboxyl group, a thiol group, a dithiopyridyl group, an α-haloacetyl group, an alkynyl group, an allyl group, a vinyl group, an amino group, an oxyamino group, a hydrazide group, and an azide group.

[13] A degradable polyethylene glycol derivative-bonded bio-related substance represented by the following formula (4):

$$[D^1-L^{11}-(CH_2CH_2O)_{n1}-L^3]_{a1}-W^1-L^5-Q-L^6-W^2-[L^4-(OCH_2CH_2)_{n2}-L^{12}-D^2]_{a2} \quad \text{formula (4)}$$

wherein n1 and n2 are each independently 45-950, $W^1$ and $W^2$ are each independently an oligopeptide of 2-47 residues, a1 and a2 are each independently 1-8, Q is a hydrocarbon chain having 2-12 carbon atoms and optionally containing an oxygen atom or a nitrogen atom, $D^1$ and $D^2$ are each independently a bio-related substance, and $L^3$, $L^4$, $L^5$, $L^6$, $L^{11}$ and $L^{12}$ are each independently a divalent spacer.

[14] The bio-related substance of [13], wherein $L^{11}$ and $L^{12}$ are each independently a urethane bond, an amide bond, an ether bond, a thioether bond, a secondary amino group, a carbonyl group, a urea bond, a triazolyl group, a bond of maleimide and mercapto, an oxime bond, or an alkylene group optionally comprising such bond and group.

[15] The bio-related substance of any one of [13]-[14], wherein the bio-related substance for D is a hormone, a cytokine, an antibody, an aptamer or an enzyme.

Advantageous Effects of Invention

The multi-arm degradable polyethylene glycol derivative of the present invention has, in its structure, an oligopeptide which is stable in blood in the body and degraded by intracellular enzymes. Therefore, the degradable polyethylene glycol derivative is stable in blood and can impart a half-life in blood that is equivalent to that of a conventional polyethylene glycol derivative without degradability to a bio-related substance. Furthermore, when the degradable polyethylene glycol derivative is incorporated into cells, the oligopeptide site of the degradable polyethylene glycol derivative is rapidly degraded, thus suppressing the generation of vacuoles in cells which has been a problem to date. In addition, since the polyethylene glycol derivative has plural functional groups, it can characteristically introduce plural bio-related substances into one molecule, and can enhance the pharmacological activity thereof. In addition, impurities developed in the production step can be reduced by using glycine as a C-terminal amino acid of oligopeptide, whereby the multi-arm degradable polyethylene glycol derivative of the present invention can be produced industrially.

DESCRIPTION OF EMBODIMENTS

The present invention is explained in detail in the following.

The degradable polyethylene glycol derivative of the present invention is represented by the following formula (1).

$$[X^1-L^1-(CH_2CH_2O)_{n1}-L^3]_{a1}-W^1-L^5-Q-L^6-W^2-[L^4-(OCH_2CH_2)_{n2}-L^2-X^2]_{a2} \quad \text{formula (1)}$$

wherein n1 and n2 are each independently 45-950, $W^1$ and $W^2$ are each independently an oligopeptide of 2-47 residues, a1 and a2 are each independently 1-8, Q is a hydrocarbon chain having 2-12 carbon atoms and optionally containing an oxygen atom or a nitrogen atom, $X^1$ and $X^2$ are each independently a functional group capable of reacting with a bio-related substance, and $L^1, L^2, L^3, L^4, L^5$ and $L^6$ are each independently a divalent spacer.

The total molecular weight of the polyethylene glycol derivative of the formula (1) of the present invention is generally 4,000-160,000, preferably 10,000-120,000, further preferably 20,000-80,000. In one preferred embodiment of the present invention, the total molecular weight of the polyethylene glycol derivative of the formula (1) of the present invention is not less than 20,000. The molecular weight here is a number average molecular weight (Mn).

n1 and n2 in the formula (1) are each a repeating unit number of polyethylene glycol. Generally, they are each independently 45-950, preferably each independently 110-690, further preferably each independently 220-460.

a1 and a2 in the formula (1) are each the number of polyethylene glycol chains bonded to oligopeptide for $W^1$ and $W^2$, respectively. Generally, they are each independently 1-8, preferably each independently 1 or 2 or 4 or 8, further preferably each independently 1 or 2 or 4.

In the formula (1), $W^1$ and $W^2$ are not particularly limited as long as each is independently an oligopeptide of 2-47 residues, preferably 2-23 residues, more preferably 2-19 residues, stable in the blood of living organisms, and is degraded by enzymes in cells. It is preferable to combine a degradable peptide and a dendrimer-like oligopeptide having an ionic amino acid (glutamic acid, aspartic acid, lysine) or a branched skeleton. When a polyethylene glycol chain is introduced into an oligopeptide, if amino group, carboxyl group, thiol group, hydroxyl group, and the like derived from the amino acids constituting the oligopeptide are mixed, the reaction cannot be controlled. Therefore, it is preferable to use an oligopeptide that can protect either an amino group or a carboxyl group and does not have cysteine or serine.

In the formula (1), Q is not particularly limited as long as it is a hydrocarbon chain having 2-12, preferably 2-8, more preferably 2-4, carbon atoms and optionally containing an oxygen atom and/or a nitrogen atom. It is preferably an alkylene group optionally containing an ether bond. As the alkylene group, ethylene group, propylene group, butylene group, pentylene group, hexylene group, heptylene group, or octylene group is preferred, and ethylene group, propylene group, or butylene group is more preferred.

Particularly preferred embodiments of Q are shown in the following Group (I).

Group (I):

$$—(CH_2)_f— \quad (q1)$$

$$—(CH_2)_f—O—(CH_2)_f— \quad (q2)$$

$$—(CH_2)_f—NH—(CH_2)_f— \quad (q3)$$

In (q1)-(q3), f is an integer of 2-12, preferably an integer of 2-8, further preferably an integer of 2-4. In (q2)-(q3), each f may be the same or different.

In the formula (1), $L^1, L^2, L^3, L^4, L^5$ and $L^6$ are each independently a divalent spacer, and these spacers are not particularly limited as long as they are groups capable of forming a covalent bond.

$L^1$ and $L^2$ are each a spacer connecting a polyethylene glycol chain and a functional group, preferably, amide bond, ether bond, thioether bond, urethane bond, secondary amino group, carbonyl group, urea bond, or alkylene group optionally containing such bond and/or group.

$L^3$ and $L^4$ are each a spacer connecting a polyethylene glycol chain and oligopeptide, preferably an alkylene group; or an alkylene group containing at least one bond and/or one group, each selected from amide bond, ether bond, thioether bond, urethane bond, secondary amino group, carbonyl group, and urea bond. $L^3$ and $L^4$ are preferably bonded to the repeating unit of polyethylene glycol via a carbon atom.

$L^5$ and $L^6$ are each a spacer connecting hydrocarbon chain Q and oligopeptide, preferably, amide bond, ether bond, thioether bond, urethane bond, secondary amino group, carbonyl group, urea bond, or alkylene group optionally containing such bond and/or group.

Particularly preferred embodiments of $L^1, L^2, L^3, L^4, L^5$ and $L^6$ are shown in the following Group (II). Two to four spacers of Group (II) may be used in combination. An ester bond and a carbonate bond are not suitable as the divalent spacers since they are gradually degraded in the blood of living organisms.

Group (II):

$$—(CH_2)_5— \quad (z1)$$

$$—(CH_2)_5—O—(CH_2)_5— \quad (z2)$$

$$—(CH_2)_5—NH—\underset{O}{\overset{\|}{C}}—(CH_2)_5— \quad (z3)$$

$$—(CH_2)_5—NH—\underset{O}{\overset{\|}{C}}—O—(CH_2)_5— \quad (z4)$$

$$—(CH_2)_5—NH—(CH_2)_5— \quad (z5)$$

$$—(CH_2)_5—\underset{O}{\overset{\|}{C}}—(CH_2)_5— \quad (z6)$$

$$—(CH_2)_5—NH—\underset{O}{\overset{\|}{C}}—(CH_2)_5—\underset{O}{\overset{\|}{C}}—NH—(CH_2)_5— \quad (z7)$$

$$—(CH_2)_5—NH—\underset{O}{\overset{\|}{C}}—(CH_2)_5—O—\underset{O}{\overset{\|}{C}}—NH—(CH_2)_5— \quad (z8)$$

$$—(CH_2)_5—\underset{O}{\overset{\|}{C}}—(CH_2)_5—\underset{O}{\overset{\|}{C}}—NH—(CH_2)_5— \quad (z9)$$

$$—(CH_2)_5—\underset{O}{\overset{\|}{C}}—(CH_2)_5—O—\underset{O}{\overset{\|}{C}}—NH—(CH_2)_5— \quad (z10)$$

$$—(CH_2)_5—O—(CH_2)_5—NH—(CH_2)_5— \quad (z11)$$

In (z1)-(z11), s is an integer of 0-10, preferably an integer of 0-6, further preferably an integer of 0-3. In (z2)-(z11), each s may be the same or different.

In the formula (1), $L^1$ and $L^2$ are preferably a combination of (z2), (z3), (z4), (z6), (z7), (z8), (z9), (z10) or (z2), and (z4), more preferably a combination of (z3), (z6), (z9), (z10) or (z2), and (z4), in Group (II).

In the formula (1), $L^3$ and $L^4$ are each preferably a group represented by (z1), (z2), (z3), (z4), (z5), (z6), (z7), (z8) or (z11), more preferably a group represented by (z3), (z5) or (z11), in Group (II).

In the formula (1), $L^5$ and $L^6$ are each preferably a group represented by (z3), (z4), (z6), (z7), (z8), (z9) or (z10), more preferably a group represented by (z3), (z6), (z9) or (z10), in Group (II).

In the formula (1), $X^1$ and $X^2$ are not particularly limited as long as each is a functional group that reacts with a functional group present in bio-related substances such as a physiologically active protein, peptide, antibody, nucleic acid, or anticancer agent to be chemically modified to form a covalent bond. For example, the functional groups described in "Harris, J. M. Poly (Ethylene Glycol) Chemistry; Plenum Press: New York, 1992", "Hermanson, G. T. Bioconjugate Techniques, 2nd ed.; Academic Press: San Diego, CA, 2008" and "PEGylated Protein Drugs: Basic Science and Clinical Applications; Veronese, F. M., Ed.; Birkhauser: Basel, Switzerland, 2009" and the like can be mentioned.

In the formula (1), the "functional group capable of reacting with a bio-related substance" for $X^1$ or $X^2$ is not particularly limited as long as it is a functional group that can be chemically bonded to a functional group of a bio-related substance such as amino group, mercapto group, aldehyde group, carboxyl group, unsaturated bond or azide group and the like.

Specifically, active ester group, active carbonate group, aldehyde group, isocyanate group, isothiocyanate group, epoxide group, carboxyl group, mercapto group, maleimide group, substituted maleimide group, hydrazide group, dithiopyridyl group, substituted sulfonate group, vinylsulfonyl group, amino group, oxyamino group ($H_2N$—O— group), iodoacetamide group, alkylcarbonyl group, alkenyl group (e.g., allyl group, vinyl group), alkynyl group, substituted alkynyl group (e.g., alkynyl group substituted by hydrocarbon group with carbon number of 1-5 to be described later), azide group, acrylic group, sulfonyloxy group (e.g., alkylsulfonyloxy group), α-haloacetyl group and the like can be mentioned. It is preferably active ester group, active carbonate group, aldehyde group, isocyanate group, isothiocyanate group, epoxide group, maleimide group, substituted maleimide group, vinylsulfonyl group, acrylic group, sulfonyloxy group (e.g., alkyl-sulfonyloxy group with carbon number of 1-5), substituted sulfonate group, carboxyl group, mercapto group, pyridyldithio group, α-haloacetyl group, alkynyl group, substituted alkynyl group (e.g., alkynyl group with carbon number of 2-5 and substituted by hydrocarbon group with carbon number of 1-5 to be described later), allyl group, vinyl group, amino group, oxyamino group, hydrazide group or azide group, more preferably active ester group, active carbonate group, aldehyde group, maleimide group, carboxyl group, oxyamino group, or amino group, particularly preferably aldehyde group, maleimide group, carboxyl group, or oxyamino group.

In another preferred embodiment, the functional groups $X^1$ and $X^2$ can be classified into the following Group (III), Group (IV), Group (V), Group (VI), Group (VII) and Group (VIII).

Group (III): functional group capable of reacting with amino group of bio-related substance The groups represented by the following (a), (b), (c), (d), (e), (f), (g), (j) and (k) can be mentioned.

Group (IV): functional group capable of reacting with mercapto group of bio-related substance The groups represented by the following (a), (b), (c), (d), (e), (f), (g), (h), (i), (j), (k) and (l) can be mentioned.

Group (V): functional group capable of reacting with aldehyde group of bio-related substance The groups represented by the following (h), (m), (n) and (p) can be mentioned.

Group (VI): functional group capable of reacting with carboxyl group of bio-related substance The groups represented by the following (h), (m), (n) and (p) can be mentioned.

Group (VII): functional group capable of reacting with unsaturated bond of bio-related substance The groups represented by the following (h), (m) and (o) can be mentioned.

Group (VIII): functional group capable of reacting with azide group of bio-related substance The group represented by the following (l) can be mentioned.

-continued $$-\overset{O}{\underset{\|}{C}}-CH_2-U_1 \quad (j)$$

$$-O-\overset{O}{\underset{\underset{\|}{O}}{S}}-Y^2 \quad (k)$$

$$-C\equiv C-Y^3 \quad (l)$$

$$-NH_2 \quad (m)$$

$$-ONH_2 \quad (n)$$

$$-N_3 \quad (o)$$

$$-\overset{O}{\underset{\|}{C}}-\overset{H}{\underset{|}{N}}-NH_2 \quad (p)$$

In functional group (j), $U_1$ is a halogen atom such as a chlorine atom (Cl), a bromine atom (Br) or an iodine atom (I), preferably Br or I, more preferably I.

In functional group (e) and functional group (l), $Y^1$ and $Y^3$ are each independently a hydrogen atom or a hydrocarbon group having 1 to 5 carbon atoms, preferably a hydrocarbon group having 1 to 5 carbon atoms. Specific examples of the hydrocarbon group having 1 to 5 carbon atoms include a methyl group, an ethyl group, a propyl group, an isopropyl group, a butyl group, a tertiary butyl group and the like, preferably a methyl group or an ethyl group.

In functional group (k), $Y^2$ is a hydrocarbon group having 1-10 carbon atoms and optionally containing a fluorine atom. Specifically, it is a methyl group, an ethyl group, a propyl group, an isopropyl group, a butyl group, a tertiary butyl group, a hexyl group, a nonyl group, a vinyl group, a phenyl group, a benzyl group, a 4-methylphenyl group, a trifluoromethyl group, a 2,2,2-trifluoroethyl group, a 4-(trifluoromethoxy)phenyl group or the like, preferably a methyl group, a vinyl group, a 4-methylphenyl group, or a 2,2,2-trifluoroethyl group.

The active ester group is an ester group having an alkoxy group with high elimination ability. As the alkoxy group with high elimination ability, an alkoxy group induced from nitrophenol, N-hydroxysuccinimide, pentafluorophenol and the like can be mentioned. The active ester group is preferably an ester group having an alkoxy group induced from N-hydroxysuccinimide.

The active carbonate group is a carbonate group having an alkoxy group with high elimination ability. As the alkoxy group with high elimination ability, an alkoxy group induced from nitrophenol, N-hydroxysuccinimide, pentafluorophenol and the like can be mentioned. The active carbonate group is preferably a carbonate group having an alkoxy group-induced from nitrophenol or N-hydroxysuccinimide.

The substituted maleimide group is a maleimide group in which a hydrocarbon group is bonded to one carbon atom of the double bond of the maleimide group. The hydrocarbon group is specifically a methyl group, an ethyl group, a propyl group, an isopropyl group, a butyl group, a tertiary butyl group and the like, preferably a methyl group or an ethyl group.

The substituted sulfonate group is a sulfonate group in which a hydrocarbon group which may contain a fluorine atom is bonded to a sulfur atom of the sulfonate group. As the hydrocarbon group which may contain a fluorine atom, specifically, a methyl group, an ethyl group, a propyl group, an isopropyl group, a butyl group, a tertiary butyl group, a hexyl group, a nonyl group, a vinyl group, a phenyl group, a benzyl group, a 4-methylphenyl group, a trifluoromethyl group, a 2,2,2-trifluoroethyl group, a 4-(trifluoromethoxy)phenyl group and the like can be mentioned. It is preferably a methyl group, a vinyl group, a 4-methylphenyl group, or a 2,2,2-trifluoroethyl group.

In the following, a degradable polyethylene glycol derivative showing a preferred embodiment of the present invention is represented by the following formula (2).

Following Formula (2):

$$X^1-L^1-(CH_2CH_2O)_{\overline{n3}}-L^3-W^3-L^5-Q-L^6-W^4-L^4-(OCH_2CH_2)_{\overline{n4}}-L^2-X^2 \quad \text{formula (2)}$$

wherein n3 and n4 are each independently 110-950, $W^3$ and $W^4$ are each independently an oligopeptide of 2-5 residues, and Q, $X^1$ and $X^2$, $L^1$, $L^2$, $L^3$, $L^4$, $L^5$ and $L^6$ are as defined above.

The total molecular weight of the polyethylene glycol derivative of the formula (2) of the present invention is generally 4,000-160,000, preferably 10,000-120,000, further preferably 20,000-80,000. In one preferred embodiment of the present invention, the total molecular weight of the polyethylene glycol derivative of the formula (2) of the present invention is not less than 20,000. The molecular weight here is a number average molecular weight (Mn).

In the formula (2), n3 and n4 are each a repeating unit number of polyethylene glycol. Generally, they are each independently 110-950, preferably each independently 220-690, further preferably each independently 220-460.

In the formula (2), $W^3$ and $W^4$ are each independently an oligopeptide of 2-5 residues, and are not particularly limited as long as it is an oligopeptide stable in the blood of living organisms and degraded by enzyme in cells. Each is preferably an oligopeptide composed of neutral amino acids not including an amino acid having an amino group or a carboxyl group in the side chain, specifically, lysine, aspartic acid, or glutamic acid. In the synthesis of the degradable polyethylene glycol derivative of the formula (2) of the present invention, the C-terminal carboxyl group of oligopeptide is utilized for the condensation reaction with a polyethylene glycol derivative when the polyethylene glycol derivative as a starting material is bonded to the oligopeptide as a starting material by reaction. However, when the oligopeptide has an amino acid having an amino group or a carboxyl group in the side chain, a side reaction between the oligopeptides, and impurities in which the polyethylene glycol derivative is introduced into the side chain carboxyl group rather than the desired C-terminal carboxyl group are developed as a result of the condensation reaction.

Since this impurity is difficult to remove by a purification step such as general extraction or crystallization, to obtain the desired product with high purity, it is desirable to use an oligopeptide composed of amino acids having no amino group or carboxyl group in the side chain. The amino acid constituting $W^3$ and $W^4$ is α-amino acid and is basically in the L form.

Cysteine, which is a neutral amino acid, has a mercapto group and forms a disulfide bond with other mercapto groups. Thus, $W^3$ and $W^4$ are each desirably an oligopeptide composed of neutral amino acids not including cysteine.

In addition, $W^3$ and $W^4$ are each preferably an oligopeptide having glycine as the C-terminal amino acid. When a C-terminal carboxyl group is reacted with a polyethylene glycol derivative, it is basically necessary to activate the C-terminal carboxyl group with a condensing agent and the like. It is known that epimerization tends to occur in amino acids other than glycine and stereoisomer is by-produced in this activation step. By using an achiral glycine as the C-terminal amino acid of the oligopeptide, a highly pure target product free from by-production of stereoisomer can be obtained.

Furthermore, $W^3$ and $W^4$ are each preferably an oligopeptide having at least one hydrophobic neutral amino acid having a hydropathy index of not less than 2.5, specifically, phenylalanine, leucine, valine, or isoleucine, more preferably an oligopeptide having phenylalanine. The hydropathic index (hydropathy index) created by Kyte and Doolittle that quantitatively indicates the hydrophobicity of amino acid shows that the larger the value, the more hydrophobic the amino acid (Kyte J & Doolittle R F, 1982, J Mol Biol, 157:105-132).

$W^3$ and $W^4$ are not particularly limited as long as each is an oligopeptide with 2-5 residues composed of neutral amino acids excluding cysteine, is stable in the blood of living organisms, and has property of degradation by an enzyme in cells. Specific examples include glycine-phenylalanine-leucine-glycine, glycine-glycine-phenylalanine-glycine, glycine-phenylalanine-glycine, glycine-leucine-glycine, valine-citrulline-glycine, valine-alanine-glycine, phenylalanine-glycine and the like, preferably glycine-phenylalanine-leucine-glycine, glycine-glycine-phenylalanine-glycine, glycine-phenylalanine-glycine, valine-citrulline-glycine, valine-alanine-glycine, or phenylalanine-glycine, more preferably glycine-phenylalanine-leucine-glycine, glycine-phenylalanine-glycine, valine-citrulline-glycine, or phenylalanine-glycine, further more preferably glycine-phenylalanine-leucine-glycine, or phenylalanine-glycine.

In the following, a degradable polyethylene glycol derivative showing a preferred embodiment of the present invention is represented by the following formula (3).
Following Formula (3):

$$[X^1-L^1-(CH_2CH_2O)_{n1}-L^3]_{b1}-W^5-L^5-Q-L^6-W^6-[L^4-(OCH_2CH_2)_{n2}-L^2-X^2]_{b2} \quad \text{formula (3)}$$

wherein $W^5$ and $W^6$ are each independently an oligopeptide consisting of 5 to 47 residues and having a symmetrical structure centered on glutamic acid, b1 and b2 are each independently 2-8, and n1 and n2, Q, $X^1$ and $X^2$, $L^1$, $L^2$, $L^3$, $L^4$, $L^5$ and $L^6$ are as defined above.

In the formula (3), b1 and b2 are each the number of polyethylene glycol chains bonded to oligopeptide for $W^5$ and $W^6$, respectively. Generally, they are each independently 2-8, preferably each independently 2 or 4 or 8, further preferably each independently 2 or 4.

$W^5$ and $W^6$ in the formula (3) are each independently an oligopeptide of 5-47 residues, preferably 5-23 residues, more preferably 5-19 residues, having a symmetrical structure centered on glutamic acid, and are not particularly limited as long as they are oligopeptides stable in the blood of living organisms and degraded by enzyme in cells. The amino acid constituting the oligopeptide preferably consists of neutral amino acid excluding cysteine, except for glutamic acid constituting the central portion. As used herein, the oligopeptide having a symmetrical structure centered on glutamic acid means a compound in which the same peptide is bonded to the α-position carboxyl group and the γ-position carboxyl group of glutamic acid, and is an oligopeptide in which paired peptides centered on glutamic acid have a symmetrical structure. The composition ratio of the number of neutral amino acids and glutamic acids in the oligopeptide (number of neutral amino acids/number of glutamic acids) is generally 2-10, preferably 2-8, further preferably 2-6. The amino acid constituting $W^5$ and $W^6$ is basically of an L type.

Particularly preferred embodiments of $W^5$ and $W^6$ are shown in the following Group (IX).
Group (IX):

(v1)
```
        Z—
   —Glu
        Z—
```

(v2)
```
           Z—
      Glu
     /    Z—
—Glu
     \    Z—
      Glu
           Z—
```

(v3)
```
                Z—
           Glu
          /     Z—
      Glu
     /    \     Z—
    /      Glu
   /            Z—
—Glu
   \            Z—
    \      Glu
     \    /     Z—
      Glu
          \     Z—
           Glu
                Z—
``` wherein Glu is a glutamic acid residue, and Z is a degradable oligopeptide of 2-5 residues consisting of neutral amino acids excluding cysteine.

In (v1)-(v3), Z is preferably an oligopeptide composed of neutral amino acids not including an amino acid having an amino group or a carboxyl group in the side chain, specifically, lysine, aspartic acid, or glutamic acid. In the synthesis of the multiarmed and degradable polyethylene glycol derivative of the formula (3) of the present invention, the C-terminal carboxyl group of oligopeptide is utilized for the condensation reaction with a polyethylene glycol derivative when the polyethylene glycol derivative as a starting material is bonded to the oligopeptide as a starting material by reaction. However, when the oligopeptide has an amino acid having an amino group or a carboxyl group in the side chain, a side reaction between the oligopeptides, and impurities in which the polyethylene glycol derivative is introduced into the side chain carboxyl group rather than the desired C-terminal carboxyl group are developed as a result of the condensation reaction.

Since this impurity is difficult to remove by a purification step such as general extraction or crystallization, to obtain the desired product with high purity, it is desirable to use an oligopeptide composed of amino acids having no amino group or carboxyl group in the side chain. The amino acid constituting Z is α-amino acid and is basically in the L form.

Cysteine, which is a neutral amino acid, has a mercapto group and forms a disulfide bond with other mercapto groups. Thus, in (v1)-(v3), Z is desirably an oligopeptide composed of neutral amino acids not including cysteine.

In (v1)-(v3), moreover, Z is preferably an oligopeptide having glycine as the C-terminal amino acid. When a C-terminal carboxyl group is reacted with a polyethylene glycol derivative, it is basically necessary to activate the C-terminal carboxyl group with a condensing agent and the like. It is known that epimerization tends to occur in amino acids other than glycine and stereoisomer is by-produced in this activation step. By using an achiral glycine as the C-terminal amino acid of the oligopeptide, a highly pure target product free from by-production of stereoisomer can be obtained.

In (v1)-(v3), moreover, Z is preferably an oligopeptide having at least one hydrophobic neutral amino acid having a hydropathy index of not less than 2.5, specifically, phenylalanine, leucine, valine, or isoleucine, more preferably an oligopeptide having phenylalanine. The hydropathic index (hydropathy index) created by Kyte and Doolittle that quantitatively indicates the hydrophobicity of amino acid shows that the larger the value, the more hydrophobic the amino acid (Kyte J & Doolittle R F, 1982, J Mol Biol, 157:105-132).

In (v1)-(v3), Z is not particularly limited as long as it is an oligopeptide with 2-5 residues composed of neutral amino acids excluding cysteine, is stable in the blood of living organisms, and has property of degradation by an enzyme in cells. Specific examples include glycine-phenylalanine-leucine-glycine, glycine-glycine-phenylalanine-glycine, glycine-phenylalanine-glycine, glycine-leucine-glycine, valine-citrulline-glycine, valine-alanine-glycine, phenylalanine-glycine and the like, preferably glycine-phenylalanine-leucine-glycine, glycine-glycine-phenylalanine-glycine, glycine-phenylalanine-glycine, valine-citrulline-glycine, valine-alanine-glycine, or phenylalanine-glycine, more preferably glycine-phenylalanine-leucine-glycine, glycine-phenylalanine-glycine, valine-citrulline-glycine, or phenylalanine-glycine, further more preferably glycine-phenylalanine-leucine-glycine, or phenylalanine-glycine.

One of the preferred embodiments of the formula (3) is a 4-arm degradable polyethylene glycol derivative represented by the following formula (5) wherein $W^5$ and $W^6$ are each v1, and b1=2, b2=2:

$$\begin{array}{c} X^1-L^1-(CH_2CH_2O)_{n1}-L^3-Z \\ \phantom{X^1-L^1-(CH_2CH_2}\diagdown \\ X^1-L^1-(CH_2CH_2O)_{n1}-L^3-Z \end{array} Glu-L^5-Q-L^6-Glu \begin{array}{c} Z-L^4-(OCH_2CH_2)_{n2}-L^2-X^2 \\ \diagup \\ Z-L^4-(OCH_2CH_2)_{n2}-L^2-X^2 \end{array} \quad \text{formula (5)}$$

wherein Glu, Z, n1 and n2, Q, $X^1$ and $X^2$, $L^1$, $L^2$, $L^3$, $L^4$, $L^5$ and $L^6$ are as defined above.

One of the preferred embodiments of the formula (3) is an 8-arm degradable polyethylene glycol derivative represented by the following formula (6) wherein $W^5$ and $W^6$ are each v2, and b1=4, b2=4:

$$\text{formula (6)}$$

$$\begin{array}{c} X^1-L^1-(CH_2CH_2O)_{n1}-L^3-Z \\ X^1-L^1-(CH_2CH_2O)_{n1}-L^3-Z-Glu \\ X^1-L^1-(CH_2CH_2O)_{n1}-L^3-Z-Glu \\ X^1-L^1-(CH_2CH_2O)_{n1}-L^3-Z \end{array} Glu-L^5-Q-L^6-Glu \begin{array}{c} Glu-Z-L^4-(OCH_2CH_2)_{n2}-L^2-X^2 \\ \phantom{Glu-}Z-L^4-(OCH_2CH_2)_{n2}-L^2-X^2 \\ Glu-Z-L^4-(OCH_2CH_2)_{n2}-L^2-X^2 \\ \phantom{Glu-}Z-L^4-(OCH_2CH_2)_{n2}-L^2-X^2 \end{array}$$

wherein Glu, Z, n1 and n2, Q, $X^1$ and $X^2$, $L^1$, $L^2$, $L^3$, $L^4$, $L^5$ and $L^6$ are as defined above.

One of the preferred embodiments of the formula (3) is a 16-arm degradable polyethylene glycol derivative represented by the following formula (7) wherein $W^5$ and $W^6$ are each v3, and b1=8, b2=8:

formula (7)

$$X^1-L^1-(CH_2CH_2O)_{n1}-L^3-Z$$
$$X^1-L^1-(CH_2CH_2O)_{n1}-L^3-Z-Glu$$
$$X^1-L^1-(CH_2CH_2O)_{n1}-L^3-Z-Glu$$
$$X^1-L^1-(CH_2CH_2O)_{n1}-L^3-Z$$
$$Glu-L^5-Q-L^6-Glu$$
$$X^1-L^1-(CH_2CH_2O)_{n1}-L^3-Z$$
$$X^1-L^1-(CH_2CH_2O)_{n1}-L^3-Z-Glu$$
$$X^1-L^1-(CH_2CH_2O)_{n1}-L^3-Z-Glu$$
$$X^1-L^1-(CH_2CH_2O)_{n1}-L^3-Z$$

$$Z-L^4-(OCH_2CH_2)_{n2}-L^2-X^2$$
$$Glu-Z-L^4-(OCH_2CH_2)_{n2}-L^2-X^2$$
$$Glu-Z-L^4-(OCH_2CH_2)_{n2}-L^2-X^2$$
$$Z-L^4-(OCH_2CH_2)_{n2}-L^2-X^2$$
$$Z-L^4-(OCH_2CH_2)_{n2}-L^2-X^2$$
$$Glu-Z-L^4-(OCH_2CH_2)_{n2}-L^2-X^2$$
$$Glu-Z-L^4-(OCH_2CH_2)_{n2}-L^2-X^2$$
$$Z-L^4-(OCH_2CH_2)_{n2}-L^2-X^2$$

wherein Glu, Z, n1 and n2, Q, $X^1$ and $X^2$, $L^1$, $L^2$, $L^3$, $L^4$, $L^5$ and $L^6$ are as defined above.

In the following, a bio-related substance to which a degradable polyethylene glycol derivative showing a preferred embodiment of the present invention is bound is represented by the following formula (4):
Following Formula (4):

$$[D^1-L^{11}-(CH_2CH_2O)_{n1}-L^3]_{a1}-W^1-L^5-Q-L^6-W^2-[L^4-(OCH_2CH_2)_{n2}-L^{12}-D^2]_{a2} \quad \text{formula (4)}$$

wherein $L^{11}$ and $L^{12}$ are each independently a divalent spacer, $D^1$ and $D^2$ are each independently a bio-related substance, and n1 and n2, a1 and a2, Q, $W^1$ and $W^2$, $L^3$, $L^4$, $L^5$ and $L^6$ are as defined above.

In the formula (4), $L^{11}$ and $L^{12}$ are each independently a divalent spacer. These spacers are not particularly limited as long as they are groups capable of forming a covalent bond, and each is preferably amide bond, ether bond, thioether bond, urethane bond, secondary amino group, carbonyl group, urea bond, triazolyl group, a bond of maleimide and mercapto, oxime bond, or alkylene group optionally containing such bond and/or group.

Particularly preferred embodiments of $L^{11}$ and $L^{12}$ are shown in the following Group (X). Two to five spacers of Group (X) may be used in combination. An ester bond and a carbonate bond are not suitable as the divalent spacers since they are gradually degraded in the blood of living organisms.

Group (X):

$$-(CH_2)_5- \quad (z1)$$
$$-(CH_2)_5-O-(CH_2)_5- \quad (z2)$$
$$-(CH_2)_5-NH-\underset{O}{\overset{\parallel}{C}}-(CH_2)_5- \quad (z3)$$

-continued $$-(CH_2)_5-NH-\underset{O}{\overset{\parallel}{C}}-O-(CH_2)_5- \quad (z4)$$
$$-(CH_2)_5-NH-(CH_2)_5- \quad (z5)$$

-continued $$-(CH_2)_5-\underset{O}{\overset{\parallel}{C}}-(CH_2)_5- \quad (z6)$$
$$-(CH_2)_5-NH-\underset{O}{\overset{\parallel}{C}}-(CH_2)_5-\underset{O}{\overset{\parallel}{C}}-NH-(CH_2)_5- \quad (z7)$$
$$-(CH_2)_5-NH-\underset{O}{\overset{\parallel}{C}}-(CH_2)_5-O-\underset{O}{\overset{\parallel}{C}}-NH-(CH_2)_5- \quad (z8)$$
$$-(CH_2)_5-\underset{O}{\overset{\parallel}{C}}-(CH_2)_5-\underset{O}{\overset{\parallel}{C}}-NH-(CH_2)_5- \quad (z9)$$
$$-(CH_2)_5-\underset{O}{\overset{\parallel}{C}}-(CH_2)_5-O-\underset{O}{\overset{\parallel}{C}}-NH-(CH_2)_5- \quad (z10)$$
$$-(CH_2)_5-NH-\underset{O}{\overset{\parallel}{C}}-(CH_2)_5-N\underset{\text{(succinimide)}}{}-S-(CH_2)_5- \quad (z11)$$

(z12)

$$—(CH_2)_5—\underset{\underset{O}{\|}}{C}—(CH_2)_5—N\begin{pmatrix}\text{succinimide ring with }S—(CH_2)_5—\end{pmatrix}$$

(z13)

$$—(CH_2)_5—NH—\underset{\underset{O}{\|}}{C}—(CH_2)_2—S—(CH_2)_5—$$

(z14)

$$—(CH_2)_5—\underset{\underset{O}{\|}}{C}—(CH_2)_2—S—(CH_2)_5—$$

(z15)

$$—(CH_2)_5—NH—\underset{\underset{O}{\|}}{C}—(CH_2)_5—O—\underset{\underset{O}{\|}}{C}—NH—(CH_2)_5—NH—(CH_2)_5—$$

(z16)

$$—(CH_2)_5—\underset{\underset{O}{\|}}{C}—(CH_2)_5—O—\underset{\underset{O}{\|}}{C}—NH—(CH_2)_5—NH—(CH_2)_5—$$

(z17)

$$—(CH_2)_5—\begin{pmatrix}\text{triazole}\end{pmatrix}—N—(CH_2)_5—\underset{\underset{O}{\|}}{C}—NH—(CH_2)_5—$$

(z18)

$$—(CH_2)_5—\begin{pmatrix}\text{triazole}\end{pmatrix}—N—(CH_2)_5—\underset{\underset{O}{\|}}{C}—(CH_2)_5—$$

(z19)

$$—(CH_2)_5—CH=N—O—(CH_2)_5—\underset{\underset{O}{\|}}{C}—NH—(CH_2)_5—$$

(z20)

$$—(CH_2)_5—CH=N—O—(CH_2)_5—\underset{\underset{O}{\|}}{C}—(CH_2)_5—$$

In (z1)-(z20), s is an integer of 0-10, preferably an integer of 0-6, further preferably an integer of 0-3. In (z2)-(z20), each s may be the same or different.

$L^{11}$ and $L^{12}$ in the formula (4) are each preferably a group represented by (z3), (z6), (z7)-(z20) in Group (I), more preferably a group represented by (z6), (z9), (z10), (z12), (z14), (z16), (z18) or (z20) in Group (I), further preferably a group represented by (z10), (z12), (z16) or (z20) in Group (I).

D in the formula (4) is a bio-related substance and is not particularly limited. It is a substance related to diagnosis, cure, alleviation, prophylaxis or treatment of diseases in human or other animals. Specifically, it includes proteins, peptides, nucleic acids, cells, viruses and the like, and suitable protein or peptide includes hormones, cytokines, antibodies, aptamers, enzymes and the like.

More specifically, cytokine includes interferon type I, type II, type III, interleukin, tumor necrosis factor, receptor antagonist thereof, and the like that regulate immunity. The growth factor includes erythropoietin, which is a hematopoietic factor, granulocyte colony-stimulating factor (GCSF), which is a stimulating factor, and the like. The blood coagulation factor includes factor V, factor VII, factor VIII, factor IX, factor X, factor XII and the like. The hormone includes calcitonin, insulin, analog thereof, exenatide, GLP-1, somatostatin, human growth hormone, and the like. The antibody includes full-length antibody, and Fab and svFV as antibody fragments; the aptamer includes DNA aptamer, RNA aptamer and the like; and the enzyme includes superoxide dismutase, uricase and the like. These proteins which have been genetically altered by changing the amino acid sequences thereof are also included. The above-described proteins have low stability in blood and are desirably modified with polyethylene glycol to prolong their half-life in blood.

Preferred proteins include interferon, interleukin, erythropoietin, GCSF, factor VIII, factor IX, human growth hormone, antibody fragment, and the like. Human growth hormone, interferon, GCSF, erythropoietin or antibody fragment (particularly Fab) is more preferred, and human growth hormone or GCSF is further preferred.

Preferred peptides include insulin, bivalirudin, teriparatide, exenatide, enfuvirtide, degarelix, mifamultide, nesiritide, goserelin, glatiramer, octreotide, lanreotide, icatibant, dicotinide, pramlintide, romiprostim, calcitonin, oxytocin, leuprorelin, and glucagon. More preferred are insulin, exenatide, and calcitonin (particularly salmon calcitonin).

One of the preferred embodiments of the bio-related substance represented by the formula (4) is a bio-related substance represented by the following formula (8):

$$D^1—L^{11}—(CH_2CH_2O)_{n3}—L^3—W^3—L^5—Q—L^6—W^4—L^4—(OCH_2CH_2)_{n4}—L^{12}—D^2 \qquad \text{formula (8)}$$

wherein $D^1$ and $D^2$, n3 and n4, Q, $W^3$ and $W^4$, $L^{11}$, $L^{12}$, $L^3$, $L^4$, $L^5$ and $L^6$ are as defined above.

One of the preferred embodiments of the bio-related substance represented by the formula (4) is a bio-related substance represented by the following formula (9):

$$[D^1—L^{11}—(CH_2CH_2O)_{n1}—L^3—]_{b1}—W^5—L^5—Q—L^6—W^6—[L^4—(OCH_2CH_2)_{n2}—L^{12}—D^2]_{b2} \qquad \text{formula (9)}$$

wherein $D^1$ and $D^2$, n1 and n2, b1 and b2, Q, $W^5$ and $W^6$, $L^{11}$, $L^{12}$, $L^3$, $L^4$, $L^5$ and $L^6$ are as defined above.

One of the preferred embodiments of the formula (9) is a bio-related substance to which a 4-arm degradable polyethylene glycol derivative represented by the following formula (10) wherein $W^5$ and $W^6$ are v1, and b1=2, b2=2:

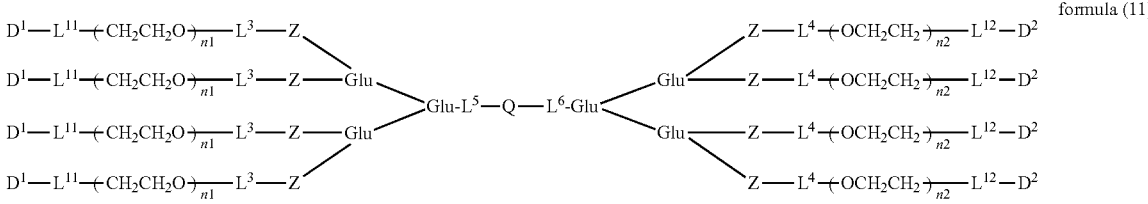

formula (10)

wherein Glu, Z, n1 and n2, Q, $D^1$ and $D^2$, $L^{11}$, $L^{12}$, $L^3$, $L^4$, $L^5$ and $L^6$ are as defined above.

One of the preferred embodiments of the formula (9) is a bio-related substance to which an 8-arm degradable polyethylene glycol derivative represented by the following formula (11) wherein $W^5$ and $W^6$ are v2, and b1=4, b2=4:

formula (11)

wherein Glu, Z, n1 and n2, Q, $D^1$ and $D^2$, $L^1$, $L^2$, $L^3$, $L^4$, $L^5$ and $L^6$ are as defined above.

One of the preferred embodiments of the formula (9) is a bio-related substance to which a 16-arm degradable polyethylene glycol derivative represented by the following formula (12) wherein $W^5$ and $W^6$ are v3, and b1=8, b2=8:

formula (12)

wherein Glu, Z, n1 and n2, Q, $D^1$ and $D^2$, $L^{11}$, $L^{12}$, $L^3$, $L^4$, $L^5$ and $L^6$ are as defined above.

Preferable examples of the degradable polyethylene glycol derivative of the formula (1) of the present invention include the following degradable polyethylene glycol derivative.

[Degradable Polyethylene Glycol Derivative (1-1)]

A degradable polyethylene glycol derivative of the formula (1), wherein n1 and n2 are each independently 220-460;

$W^1$ and $W^2$ are each independently an oligopeptide of 2-9 residues (e.g., phenylalanine-glycine, glycine-leucine-phenylalanine-glycine, glycine-phenylalanine-glutamic acid-phenylalanine-glycine, glycine-leucine-phenylalanine-glycine-glutamic acid-glycine-phenylalanine-leucine-glycine);

a1 and a2 are each independently 1, 2 or 4;

Q is an alkylene group (e.g., ethylene group, propylene group);

$X^1$ and $X^2$ are each independently selected from the group consisting of an active carbonate group (e.g., N-succinimidyl carbonate group), a maleimide group, a carboxyl group and an amino group;

$L^1$ and $L^2$ are each independently an ether bond, or an alkylene group (e.g., methylene group, ethylene group, propylene group) optionally containing an amide bond or a urethane bond;

$L^3$ and $L^4$ are each an alkylene group (e.g., propylene group) containing a secondary amino group; and $L^5$ and $L^6$ are each a carbonyl group.

Preferable examples of the degradable polyethylene glycol derivative of the formula (2) of the present invention include the following degradable polyethylene glycol derivative.

[Degradable Polyethylene Glycol Derivative (2-1)]

A degradable polyethylene glycol derivative of the formula (2), wherein n3 and n4 are each independently 220-460;

$W^3$ and $W^4$ are each independently an oligopeptide of 2-5 residues (e.g., phenylalanine-glycine, glycine-leucine-phenylalanine-glycine);

Q is an alkylene group (e.g., ethylene group, propylene group);

$X^1$ and $X^2$ are each independently selected from the group consisting of an active carbonate group (e.g., N-succinimidyl carbonate group), and a maleimide group;

$L^1$ and $L^2$ are each independently an ether bond, or an alkylene group (e.g., ethylene group, propylene group) optionally containing an amide bond;

$L^3$ and $L^4$ are each an alkylene group (e.g., propylene group) containing a secondary amino group; and $L^5$ and $L^6$ are each a carbonyl group.

Preferable examples of the degradable polyethylene glycol derivative of the formula (3) of the present invention include so the following degradable polyethylene glycol derivative.

[Degradable Polyethylene Glycol Derivative (3-1)]

A degradable polyethylene glycol derivative of the formula (3), wherein n1 and n2 are each independently 220-460;

$W^5$ and $W^6$ are each independently an oligopeptide of 5-9 residues having a symmetrical structure centered on glutamic acid (e.g., glycine-phenylalanine-glutamic acid-phenylalanine-glycine, glycine-leucine-phenylalanine-glycine-glutamic acid-glycine-phenylalanine-leucine-glycine);

b1 and b2 are each independently 2 or 4 or 8;

Q is an alkylene group (e.g., propylene group);

$X^1$ and $X^2$ are each independently selected from the group consisting of a carboxyl group, an amino group, and an oxyamino group;

$L^1$ and $L^2$ are each independently an ether bond or an alkylene group (e.g., methylene group, ethylene group) optionally containing a urethane bond;

$L^3$ and $L^4$ are each an alkylene group (e.g., propylene group) containing a secondary amino group; and $L^5$ and $L^6$ are each a carbonyl group.

The multi-arm and degradable polyethylene glycol derivative of the present invention can be produced, for example, by the following steps.

Reaction A $$Pro^1-NH-Peptide-\overset{O}{\underset{\|}{C}}-OH \quad +$$

$$NH_2-L^7-PEG-L^1-X^1-Pro^2 \longrightarrow$$

$$Pro^1-NH-Peptide-\overset{O}{\underset{\|}{C}}-NH-L^7-PEG-L^1-X^1-Pro^2$$

(1)

(in the step, PEG is a polyethylene glycol chain, Peptide is an oligopeptide, $Pro^1$ and $Pro^2$ are protecting groups, $L^7$ is a divalent spacer, and $L^1$ and $X^1$ are as defined above.)

PEG in the step is a polyethylene glycol chain, and the molecular weight thereof is as defined for the aforementioned n1 and n2 as the number of repeating units of polyethylene glycol, namely, since n1 and n2 are each independently 45-950, the molecular weight thereof is within the range of 2000-42000.

Peptide in the step is an oligopeptide defined for the aforementioned $W^3$ and $W^4$. In this step, an oligopeptide in which the N-terminal amino group is protected by a protecting group is used.

$Pro^1$ and $Pro^2$ in the step is a protecting group. A protecting group here is a component that prevents or inhibits the reaction of a particular chemically reactive functional group in a molecule under certain reaction conditions. Protecting groups vary depending on the kind of chemically reactive functional group to be protected, the conditions to be used and the presence of other functional group or protecting group in the molecule. Specific examples of the protecting group can be found in many general books, and they are described in, for example, "Wuts, P. G. M.; Greene, T. W. Protective Groups in Organic Synthesis, 4th ed.; Wiley-Interscience: New York, 2007". The functional group protected by a protecting group can be deprotected, that is, chemically reacted, using a reaction condition suitable for each protecting group, whereby the original functional group can be regenerated. Representative deprotection conditions for protecting groups are described in the aforementioned literature.

In the step, $L^7$ is the same divalent spacer as in the aforementioned $L^3$ and $L^4$.

Reaction A is a process for bonding a carboxyl group of oligopeptide with the N-terminal amino group protected by a protecting group $Pro^1$ with an amino group of a polyethylene glycol derivative, in which a functional group $X^1$ is protected by a protecting group $Pro^2$, by a condensation reaction to give polyethylene glycol derivative (1).

The protecting group $Pro^1$ of the N-terminal amino group of oligopeptide is not particularly limited. For example, an acyl protecting group and a carbamate protecting group can be mentioned, and a trifluoroacetyl group, a 9-fluorenylmethyloxycarbonyl group (Fmoc), a tert-butyloxycarbonyl group and the like can be specifically mentioned.

The protecting group $Pro^2$ of the functional group $X^1$ of the polyethylene glycol derivative is, for example, a trifluoroacetyl group, an Fmoc group, a tert-butyloxycarbonyl group or the like when $X^1$ is an amino group, a tetrahydropyranyl group, a tert-butyl group, a benzyl group or the like when $X^1$ is a hydroxyl group, and a methyl group, a tert-butyl group, a benzyl group or the like when $X^1$ is a carboxyl group. Note that the protecting groups $Pro^1$ and $Pro^2$ are different from each other.

The condensation reaction is not particularly limited, and a reaction using a condensing agent is desirable. As the condensing agent, a carbodiimide condensing agent such as dicyclohexylcarbodiimide (DCC), 1-ethyl-3-(3-dimethylaminopropyl)carbodiimide hydrochloride (EDC) or the like may be used alone, or it may be used in combination with a reagent such as N-hydroxysuccinimide (NHS), 1-hydroxybenzotriazole (HOBt), 1-hydroxy-7-azabenzotriazole (HOAt) and the like. Also, a condensing agent with higher reactivity such as HATU, HBTU, TATU, TBTU, COMU, 4-(4,6-dimethoxy-1,3,5-triazin-2-yl)-4-methylmorpholinium chloride n hydrate (DMT-MM) and the like may be used. To promote the reaction, a base such as triethylamine, dimethylaminopyridine and the like may also be used.

Impurities by-produced in the reaction, or oligopeptides and condensing agents which were not consumed and remain in the reaction are preferably removed by purification. The purification is not particularly limited, and extraction, recrystallization, adsorption treatment, reprecipitation, column chromatography, supercritical extraction, and the like can be used for purification.

Deprotection B (1) ⟶

$NH_2$—Peptide—C(=O)—NH—$L^7$—PEG—$L^1$—$X^1$—$Pro^2$ (2)

Deprotection B is a process for removing the protecting group $Pro^1$ of polyethylene glycol derivative (1) obtained in reaction A to give polyethylene glycol derivative (2). For the deprotection reaction, a conventionally-known method can be used. It is necessary to use conditions that do not cause degradation of protecting group $Pro^2$, oligopeptide, and divalent spacers for $L^1$ and $L^7$. This step can also be performed as a part of the step of reaction A.

Impurities and the like by-produced in the deprotection reaction are preferably removed by purification. The purification is not particularly limited, and extraction, recrystallization, adsorption treatment, reprecipitation, column chromatography, supercritical extraction, and the like can be used for purification.

Reaction C (2) + HOOC—$CH_2CH_2CH_2$—COOH + (2) ⟶

$Pro^2$—$X^1$—$L^1$—PEG—$L^7$—NH—C(=O)—Peptide—NH—C(=O)—$CH_2CH_2CH_2$—C(=O)—NH—Peptide—C(=O)—NH—$L^7$—PEG—$L^1$—$X^1$—$Pro^2$ (3)

In reaction C, the amino group of the polyethylene glycol derivative (2) obtained in deprotection B and the two carboxyl groups of glutaric acid are bonded by a condensation reaction to give the 2-arm polyethylene glycol derivative (3) having a structure in which two degradable polyethylene glycol chains are connected by glutaric acid.

As glutaric acid used here as a core molecule, other dibasic acids such as succinic acid, adipic acid, or sebacic acid may be used. In addition, a compound in which two hydroxyl groups of ethylene glycol, propylene glycol, butanediol, pentanediol, hexanediol, heptanediol, octanediol, nonanediol, decanediol, and the like are activated with nitrophenyl carbonate or succinimidyl carbonate may also be used.

Similar to the aforementioned reaction A, a reaction using a condensing agent is desirable and, to promote the reaction, a base such as triethylamine, dimethylaminopyridine and the like may also be used.

Impurities by-produced in the reaction, or polyethylene glycol derivative and the like which were not consumed and remain in the reaction are preferably removed by purification. The purification is not particularly limited, and extraction, recrystallization, adsorption treatment, reprecipitation, column chromatography, supercritical extraction, and the like can be used for purification.

(in the step, $Pro^3$ is a protecting group, $L^8$ is a divalent spacer, and PEG, Peptide, $Pro^1$, $L^2$ and $X^2$ are as defined above.)

In the step, $Pro^3$ is the same protecting group as in the aforementioned $Pro^1$ and $Pro^2$.

In the step, $L^8$ is the same divalent spacer as in the aforementioned $L^3$ and $L^4$.

Reaction E is a process for bonding a carboxyl group of oligopeptide with the N-terminal amino group protected by protecting group $Pro^1$ with an amino group of a polyethylene glycol derivative in which functional group $X^2$ is protected by protecting group $Pro^3$, by a condensation reaction to give polyethylene glycol derivative (5).

Similar to the aforementioned reaction A, a reaction using a condensing agent is desirable, and impurities by-produced in the reaction, or polyethylene glycol derivative and the like which were not consumed and remain in the reaction are preferably removed by purification.

Deprotection D $$(3) \longrightarrow$$

$$X^1-L^1-PEG-L^7-NH-\underset{\underset{O}{\|}}{C}-Peptide-NH-\underset{\underset{O}{\|}}{C}-CH_2CH_2CH_2-\underset{\underset{O}{\|}}{C}-NH-Peptide-\underset{\underset{O}{\|}}{C}-NH-L^7-PEG-L^1-X^1$$

(4)

Deprotection D is a process for removing the protecting group of polyethylene glycol derivative (3) obtained in reaction C to give polyethylene glycol derivative (4). For the deprotection reaction, a conventionally-known method can be used. It is necessary to use conditions that do not cause degradation of oligopeptide and divalent spacer for $L^1$ and $L^7$. This step can also be performed as a part of the step of reaction C.

Impurities and the like by-produced in the deprotection reaction are preferably removed by purification. The purification is not particularly limited, and extraction, recrystallization, adsorption treatment, reprecipitation, column chromatography, supercritical extraction, and the like can be used for purification.

By the above steps, a 2-arm polyethylene glycol derivative (4) having two functional groups $X^1$ having glutaric acid as a core molecule can be obtained.

Reaction E $$Pro^1-NH-Peptide-\underset{\underset{O}{\|}}{C}-OH \quad +$$

$$NH_2-L^8-PEG-L^2-X^2-Pro^3 \longrightarrow$$

$$Pro^1-NH-Peptide-\underset{\underset{O}{\|}}{C}-NH-L^8-PEG-L^2-X^2-Pro^3$$

(5)

Deprotection F $$(5) \longrightarrow$$

$$NH_2-Peptide-\underset{\underset{O}{\|}}{C}-NH-L^8-PEG-L^2-X^2-Pro^3$$

(6)

Deprotection F is a process for removing the protecting group $Pro^1$ of polyethylene glycol derivative (5) obtained in reaction E to give polyethylene glycol derivative (6). For the deprotection reaction, a conventionally-known method can be used. It is necessary to use conditions that do not cause degradation of protecting group $Pro^3$, oligopeptide and divalent spacer for $L^2$ and $L^8$. This step can also be performed as a part of the step of reaction E.

Impurities by-produced in the deprotection reaction, and the like are preferably removed by purification. The purification is not particularly limited, and extraction, recrystallization, adsorption treatment, reprecipitation, column chromatography, supercritical extraction, and the like can be used for purification.

Reaction G $$(6) + \text{[glutaric anhydride]} \longrightarrow \text{Pro}^3-\text{X}^2-\text{L}^2-\text{PEG}-\text{L}^8-\text{NH}-\underset{\underset{O}{\|}}{C}-\text{Peptide}-\text{NH}-\underset{\underset{O}{\|}}{C}-\text{CH}_2\text{CH}_2\text{CH}_2-\underset{\underset{O}{\|}}{C}-\text{OH} \quad (2) \longrightarrow$$

(7)

$$\text{Pro}^3-\text{X}^2-\text{L}^2-\text{PEG}-\text{L}^8-\text{NH}-\underset{\underset{O}{\|}}{C}-\text{Peptide}-\text{NH}-\underset{\underset{O}{\|}}{C}-\text{CH}_2\text{CH}_2\text{CH}_2-\underset{\underset{O}{\|}}{C}-\text{NH}-\text{Peptide}-\underset{\underset{O}{\|}}{C}-\text{NH}-\text{L}^7-\text{PEG}-\text{L}^1-\text{X}^1-\text{Pro}^2$$

(8)

In reaction G, the polyethylene glycol derivative (6) obtained in deprotection F and glutaric anhydride are reacted to give the polyethylene glycol derivative (7) having a carboxyl group. Furthermore, the amino group of the polyethylene glycol derivative (2) obtained in deprotection B and the carboxyl group of (7) are bonded by a condensation reaction to give the 2-arm polyethylene glycol derivative (8) having a structure in which two different kinds of degradable polyethylene glycol chains are connected by glutaric acid.

In reaction G, it is preferable to use a dibasic acid anhydride such as glutaric anhydride, succinic anhydride or the like, and a compound in which one of the carboxyl groups of a dibasic acid such as succinic acid, glutaric acid, adipic acid, and sebacic acid is protected by a methyl group, a tert-butyl group, a benzyl group, or the like may also be used. In addition, a compound in which one of the two hydroxyl groups of ethylene glycol, propylene glycol, butanediol, pentanediol, hexanediol, heptanediol, octanediol, nonanediol, decanediol, and the like is activated with nitrophenyl carbonate or succinimidyl carbonate, and the other hydroxyl group is protected by a tetrahydropyranyl group, a tert-butyl group, a benzyl group or the like may also be used.

Similar to the aforementioned reaction A, the reaction with (2) is desirably a reaction using a condensing agent. To promote the reaction, a base such as triethylamine, dimethylaminopyridine and the like may also be used.

Impurities by-produced in the reaction, or polyethylene glycol derivative and the like which were not consumed and remain in the reaction are preferably removed by purification. The purification is not particularly limited, and extraction, recrystallization, adsorption treatment, reprecipitation, column chromatography, supercritical extraction, and the like can be used for purification.

Deprotection H $$(8) \longrightarrow$$

$$\text{X}^2-\text{L}^2-\text{PEG}-\text{L}^8-\text{NH}-\underset{\underset{O}{\|}}{C}-\text{Peptide}-\text{NH}-\underset{\underset{O}{\|}}{C}-\text{CH}_2\text{CH}_2\text{CH}_2-\underset{\underset{O}{\|}}{C}-\text{NH}-\text{Peptide}-\underset{\underset{O}{\|}}{C}-\text{NH}-\text{L}^7-\text{PEG}-\text{L}^1-\text{X}^1$$

(9)

Deprotection H is a process for removing the protecting groups $Pro^2$ and $Pro^3$ of polyethylene glycol derivative (8) obtained in reaction G to give polyethylene glycol derivative (9). For the deprotection reaction, a conventionally-known method can be used. It is necessary to use conditions that do not cause degradation of oligopeptide and divalent spacers for $L^1$, $L^2$, $L^7$ and $L^8$. In this step, the protecting groups $Pro^2$ and $Pro^3$ may be deprotected under the same conditions, or may be deprotected in separate steps. This step can also be performed as a part of the step of reaction G.

Impurities by-produced in the deprotection reaction, and the like are preferably removed by purification. The purification is not particularly limited, and extraction, recrystallization, adsorption treatment, reprecipitation, column chromatography, supercritical extraction, and the like can be used for purification.

By the above steps, a two-arm polyethylene glycol derivative (9) having two different functional groups $X^1$ and $X^2$ having glutaric acid as a core molecule can be obtained.

Reaction I $$Pro^1-NH-Peptide-\underset{O}{\overset{\parallel}{C}}-OH \ + $$

$$NH_2-L^9-PEG-L^{10}-OH \longrightarrow$$

$$Pro^1-NH-Peptide-\underset{O}{\overset{\parallel}{C}}-NH-L^9-PEG-L^{10}-OH$$

(10)

(in the step, $L^9$ and $L^{10}$ are divalent spacers, and PEG, Peptide, and $Pro^1$ are as defined above.)

In the step, $L^9$ is the same divalent spacer as that defined for the aforementioned $L^3$ and $L^4$, and $L^{10}$ is the same divalent spacer as that defined for the aforementioned $L^1$ and $L^2$.

Reaction I is a process for bonding a carboxyl group of oligopeptide with the N-terminal amino group protected by a protecting group $Pro^1$ with an amino group of a polyethylene glycol derivative having a hydroxyl group at one terminal by a condensation reaction to give polyethylene glycol derivative (10).

Similar to the aforementioned reaction A, a reaction using a condensing agent is desirable, particularly, a reaction using a condensing agent DMT-MM or the like that selectively promotes condensation of the amino group and the carboxyl group is preferred. Impurities by-produced in the reaction, or polyethylene glycol derivative and the like which were not consumed and remain in the reaction are preferably removed by purification.

Deprotection J $$(10) \longrightarrow NH_2-Peptide-\underset{O}{\overset{\parallel}{C}}-NH-L^9-PEG-L^{10}-OH$$

(11)

Deprotection J is a process for removing the protecting group $Pro^1$ of polyethylene glycol derivative (10) obtained in reaction I to give polyethylene glycol derivative (11). For the deprotection reaction, a conventionally-known method can be used. It is necessary to use conditions that do not cause degradation of oligopeptide and divalent spacer for $L^9$ and $L^{10}$. This step can also be performed as a part of the step of reaction I.

Impurities by-produced in the deprotection reaction, and the like are preferably removed by purification. The purification is not particularly limited, and extraction, recrystallization, adsorption treatment, reprecipitation, column chromatography, supercritical extraction, and the like can be used for purification.

Reaction K $$(11) \ + \ HOOC-CH_2CH_2CH_2CH_2-COOH \ + \ (11) \longrightarrow$$

$$HO-L^{10}-PEG-L^9-NH-\underset{O}{\overset{\parallel}{C}}-Peptide-NH-\underset{O}{\overset{\parallel}{C}}-CH_2CH_2CH_2CH_2-\underset{O}{\overset{\parallel}{C}}-NH-Peptide-\underset{O}{\overset{\parallel}{C}}-NH-L^9-PEG-L^{10}-OH$$

(12)

In reaction K, the amino group of the polyethylene glycol derivative (11) obtained in deprotection J and the two carboxyl groups of adipic acid are bonded by a condensation reaction to give the 2-arm polyethylene glycol derivative (12) having a structure in which two degradable polyethylene glycol chains are connected by adipic acid.

As adipic acid used here as a core molecule, other dibasic acids such as succinic acid, glutaric acid, or sebacic acid may be used. In addition, a compound in which two hydroxyl groups of ethylene glycol, propylene glycol, butanediol, pentanediol, hexanediol, heptanediol, octanediol, nonanediol, decanediol, and the like are activated with nitrophenyl carbonate or succinimidyl carbonate may also be used.

Similar to the aforementioned reaction A, a reaction using a condensing agent is desirable. Particularly, a reaction using a condensing agent DMT-MM or the like that selectively promotes condensation of the amino group and the carboxyl group is preferred.

Impurities by-produced in the reaction, or polyethylene glycol derivative and the like which were not consumed and remain in the reaction are preferably removed by purification. The purification is not particularly limited, and extraction, recrystallization, adsorption treatment, reprecipitation, column chromatography, supercritical extraction, and the like can be used for purification.

By the above steps, a 2-arm polyethylene glycol derivative (13) having two functional groups $X^1$ having adipic acid as a core molecule can be obtained.

Reaction M $$Pro^1-\overset{H}{N}-\overset{|}{\underset{|}{C}}\begin{matrix}\diagup C(=O)-OH\\ \diagdown C(=O)-OH\end{matrix}$$

glutamic acid derivative

+

$$NH_2-Peptide-\underset{\underset{O}{\|}}{C}-NH-L^7-PEG-L^1-X^1-Pro^2 \longrightarrow$$

(2)

Reaction L

(12) ⟶

$$X^1-L^1-PEG-L^9-NH-\underset{\underset{O}{\|}}{C}-Peptide-NH-\underset{\underset{O}{\|}}{C}-CH_2CH_2CH_2CH_2-\underset{\underset{O}{\|}}{C}-NH-Peptide-\underset{\underset{O}{\|}}{C}-NH-L^9-PEG-L^1-X^1$$

(13)

Reaction L is a step of converting the two hydroxyl groups of the polyethylene glycol derivative (12) obtained in Reaction K into the functional group $X^1$ to obtain the polyethylene glycol derivative (13).

As a reaction for converting a hydroxyl group to another functional group, a conventionally known method can be used. For example, they can be converted into various functional groups by using the methods described in "Harris, J. M. Poly(Ethylene Glycol) Chemistry; Plenum Press: New York, 1992", "Hermanson, G. T. Bioconjugate Techniques, 2nd ed.; Academic Press: San Diego, CA, 2008", "PEGylated Protein Drugs: Basic Science and Clinical Applications; Veronese, F. M., Ed.; Birkhauser: Basel, Switzerland, 2009", and the like.

For example, the hydroxyl group of (12) can be converted to an activated carbonate group by reacting a reaction reagent such as para-nitrophenyl chloroformate or disuccinimidyl carbonate with (12) using a base such as triethylamine. In addition, the hydroxyl group of (12) can be converted to an amino group or an oxyamino group by the method described in JP-B-5418360.

The reaction reagent used in reaction L is a low-molecular-weight reagent and has solubility vastly different from that of polyethylene glycol derivatives, which are high-molecular-weight polymers. Thus, it can be easily removed by general purification methods such as extraction and crystallization. The purification is not particularly limited, and extraction, recrystallization, adsorption treatment, reprecipitation, column chromatography, supercritical extraction, and the like can be used for purification.

-continued $$Pro^1-\overset{H}{N}-\overset{|}{\underset{|}{C}}\begin{matrix}\diagup C(=O)-NH-Peptide-\underset{\underset{O}{\|}}{C}-NH-L^7-PEG-L^1-X^1-Pro^2\\ \diagdown C(=O)-NH-Peptide-\underset{\underset{O}{\|}}{C}-NH-L^7-PEG-L^1-X^1-Pro^2\end{matrix}$$

(14)

In reaction M, the amino group of the polyethylene glycol derivative (2) obtained in deprotection B and the two carboxyl groups of the glutamic acid derivative whose amino group is protected by a protecting group are bonded by a condensation reaction to give the branched polyethylene glycol derivative (14) having a structure in which two degradable polyethylene glycol chains are connected by a glutamic acid residue.

Similar to the aforementioned reaction A, a reaction using a condensing agent is desirable and to promote the reaction, a base such as triethylamine, dimethylaminopyridine and the like may also be used.

The protecting group of amino group of glutamic acid is not particularly limited and, for example, an acyl protecting group and a carbamate protecting group can be mentioned, and a trifluoroacetyl group, a 9-fluorenylmethyloxycarbonyl group (Fmoc), a tert-butyloxycarbonyl group and the like can be specifically mentioned.

Impurities by-produced in the reaction, or polyethylene glycol derivative and the like which were not consumed and remain in the reaction are preferably removed by purification. The purification is not particularly limited, and extraction, recrystallization, adsorption treatment, reprecipitation, column chromatography, supercritical extraction, and the like can be used for purification.

Deprotection N is a process for removing the protecting group of polyethylene glycol derivative (14) obtained in reaction M to give polyethylene glycol derivative (15). For the deprotection reaction, a conventionally-known method can be used. It is necessary to use conditions that do not cause degradation of oligopeptide and divalent spacer for $L^1$ and $L^7$. This step can also be performed as a part of the step of reaction M.

Deprotection N

(14) →

$$H_2N-\underset{\underset{(15)}{\phantom{X}}}{\overset{\overset{O}{\|}}{\underset{\|}{C}}}\begin{matrix}-NH-Peptide-\underset{\|}{\overset{\|}{C}}-NH-L^7-PEG-L^1-X^1-Pro^2\\ O\\ -NH-Peptide-\underset{\|}{\overset{\|}{C}}-NH-L^7-PEG-L^1-X^1-Pro^2\\ O\end{matrix}$$

Impurities by-produced in the deprotection reaction, and the like are preferably removed by purification. The purification is not particularly limited, and extraction, recrystallization, adsorption treatment, reprecipitation, column chromatography, supercritical extraction, and the like can be used for purification.

Reaction O

(15) + HOOC—CH$_2$CH$_2$CH$_2$—COOH + (15) ⟶

$$Pro^2-X^1-L^1-PEG-L^7-NH-\underset{\|}{\overset{\|}{C}}-Peptide-NH-\underset{O}{\overset{O}{\|\|}}\cdots NH-\underset{O}{\overset{\|}{C}}-CH_2CH_2CH_2-\underset{O}{\overset{\|}{C}}-HN\cdots -NH-Peptide-\underset{\|}{\overset{\|}{C}}-NH-L^7-PEG-L^1-X^1-Pro^2$$

(16)

In reaction O, the amino group of the polyethylene glycol derivative (15) obtained in deprotection N and the two carboxyl groups of glutaric acid are bonded by a condensation reaction to give the 4-arm polyethylene glycol derivative (16) having a structure in which four degradable polyethylene glycol chains are connected by glutaric acid.

As glutaric acid used here as a core molecule, other dibasic acids such as succinic acid, adipic acid, or sebacic acid may be used. In addition, a compound in which two hydroxyl groups of ethylene glycol, propylene glycol, butanediol, pentanediol, hexanediol, heptanediol, octanediol, nonanediol, decanediol, and the like are activated with nitrophenyl carbonate or succinimidyl carbonate may also be used.

Similar to the aforementioned reaction A, a reaction using a condensing agent is desirable and, to promote the reaction, a base such as triethylamine, dimethylaminopyridine and the like may also be used.

Impurities by-produced in the reaction, or polyethylene glycol derivative and the like which were not consumed and remain in the reaction are preferably removed by purification. The purification is not particularly limited, and extraction, recrystallization, adsorption treatment, reprecipitation, column chromatography, supercritical extraction, and the like can be used for purification.

Deprotection P

(16) ⟶

$$X^1-L^1-PEG-L^7-NH-\underset{\underset{O}{\|}}{C}-Peptide-NH-\overset{O}{\underset{}{\|}}...NH-\underset{\underset{O}{\|}}{C}-CH_2CH_2CH_2-\underset{\underset{O}{\|}}{C}-HN...NH-Peptide-\underset{\underset{O}{\|}}{C}-NH-L^7-PEG-L^1-X^1$$

(17)

Deprotection P is a process for removing the protecting group of polyethylene glycol derivative (16) obtained in reaction O to give polyethylene glycol derivative (17). For the deprotection reaction, a conventionally-known method can be used. It is necessary to use conditions that do not cause degradation of oligopeptide and divalent spacer for $L^1$ and $L^7$. This step can also be performed as a part of the step of reaction O.

Impurities by-produced in the deprotection reaction, and the like are preferably removed by purification. The purification is not particularly limited, and extraction, recrystallization, adsorption treatment, reprecipitation, column chromatography, supercritical extraction, and the like can be used for purification.

By the above steps, a 4-arm polyethylene glycol derivative (17) having four functional groups $X^1$ having glutaric acid as a core molecule can be obtained.

Reaction Q

[glutamic acid derivative structure: Pro—NH—CH(CH2CH2COOH)—COOH] + (15) → glutamic acid derivative

[Structure (18): branched structure with Pro—NH—glutamic acid core linking four —NH—Peptide—C(=O)—NH—L⁷—PEG—L¹—X¹—Pro² chains through glutamic acid residues]

(18)

Reaction Q is a process for bonding an amino group of polyethylene glycol derivative (15) obtained in deprotection N, and two carboxyl groups of a glutamic acid derivative in which an amino group is protected by a protecting group by a condensation reaction to give branched polyethylene glycol derivative (18) having a structure in which four degradable polyethylene glycol chains are linked by a glutamic acid residue.

The reaction and purification can be performed under the same conditions as in the aforementioned reaction M.

As a method for removing polyethylene glycol impurities having different molecular weight and different functional group from polyethylene glycol derivative (18), the purification techniques described in JP-A-2014-208786, JP-A-2011-79934 can be used.

Deprotection R

(18) ⟶

[Structure (19): A branched molecule with H₂N-group on a lysine-like core connecting to four branches, each of structure: —NH—Peptide—C(=O)—NH—L⁷—PEG—L¹—X¹—Pro²]

Deprotection R is a process for removing the protecting group of polyethylene glycol derivative (18) obtained in reaction Q to give polyethylene glycol derivative (19). For the deprotection reaction, a conventionally-known method can be used. It is necessary to use conditions that do not cause degradation of oligopeptide and divalent spacer for $L^1$ and $L^7$. The reaction and purification can be performed under the same conditions as in the aforementioned deprotection N. This step can also be performed as a part of the step of reaction Q.

Reaction S

(19) + HOOC—CH₂CH₂CH₂—COOH + (19) ⟶

[Structure (20): Two units of (19) joined via a glutaric acid linker (—C(=O)—CH₂CH₂CH₂—C(=O)—) connecting the two H₂N termini through amide bonds, giving eight branches total each terminating in Pro²—X¹—L¹—PEG—L⁷—NH—C(=O)—Peptide—NH—]

Reaction S is a process for bonding an amino group of polyethylene glycol derivative (19) obtained in deprotection R, and two carboxyl groups of glutaric acid by a condensation reaction to give 8-arm polyethylene glycol derivative (20) having a structure in which eight degradable polyethylene glycol chains are linked by glutalic acid.

As glutaric acid used here as a core molecule, other dibasic acids such as succinic acid, adipic acid, or sebacic acid may be used. In addition, a compound in which two hydroxyl groups of ethylene glycol, propylene glycol, butanediol, pentanediol, hexanediol, heptanediol, octanediol, nonanediol, decanediol, and the like are activated with nitrophenyl carbonate or succinimidyl carbonate may also be used.

Similar to the aforementioned reaction A, a reaction using a condensing agent is desirable and, to promote the reaction, a base such as triethylamine, dimethylaminopyridine and the like may also be used.

Impurities by-produced in the reaction, or polyethylene glycol derivative and the like which were not consumed and remain in the reaction are preferably removed by purification. The purification is not particularly limited, and extraction, recrystallization, adsorption treatment, reprecipitation, column chromatography, supercritical extraction, and the like can be used for purification.

The polyethylene glycol derivatives (4), (9), (17) and (21) obtained in deprotection D, deprotection H, deprotection P and deprotection T have functional groups $X^1$ and $X^2$. Utilizing these functional groups, conversion to various functional groups is possible.

For example, when the functional groups $X^1$ and $X^2$ are amino groups, there is no particular limitation, but basically, conversion to various functional groups can be easily performed using a compound having an active ester group capable of reacting with an amino group, or a general reaction reagent such as acid anhydride, acid chloride, or the like.

Specifically, when conversion of an amino group to a maleimide group is desired, the desired product can be obtained by reacting with the following reagents.

Deprotection T

(20) →

(21)

Deprotection T is a process for removing the protecting group of polyethylene glycol derivative (20) obtained in reaction S to give polyethylene glycol derivative (21). For the deprotection reaction, a conventionally-known method can be used. It is necessary to use conditions that do not cause degradation of oligopeptide and divalent spacer for $L^1$ and $L^7$. This step can also be performed as a part of the step of reaction S.

Impurities by-produced in the deprotection reaction, and the like are preferably removed by purification. The purification is not particularly limited, and extraction, recrystallization, adsorption treatment, reprecipitation, column chromatography, supercritical extraction, and the like can be used for purification.

By the above steps, an 8-arm polyethylene glycol derivative (21) having eight functional groups $X^1$ having glutaric acid as a core molecule can be obtained.

For example, when conversion of the terminal amino group of a polyethylene glycol derivative to a carboxyl group is desired, the desired product can be obtained by reacting with succinic anhydride or glutaric anhydride.

For example, when conversion of the terminal amino group of a polyethylene glycol derivative to a hydroxyl group is desired, the desired product can be obtained by condensation reacting with a ring-opening product of cyclic ester such as caprolactone and the like.

Since these reaction reagents are low-molecular-weight reagents and have solubility vastly different from that of polyethylene glycol derivatives, which are high-molecular-weight polymers, they can be easily removed by general purification methods such as extraction and crystallization.

The degradable polyethylene glycol obtained through the above steps is required to be stable in blood and have the property of being degraded only in cells. To properly evaluate the property, for example, the following test is performed, based on which the stability in blood and degradability in cells of the degradable polyethylene glycol can be evaluated.

In consideration of the influence of the kind of the functional group of the polyethylene glycol derivative in these evaluations, all the evaluation samples used for the tests were polyethylene glycol derivatives having one amino group.

The test method for evaluating the stability of degradable polyethylene glycol derivative in blood is not particularly limited. For example, a test using serum of mouse, rat, human or the like can be mentioned. Specifically, a polyethylene glycol derivative is dissolved in serum to a concentration of 1-10 mg/mL, incubated at 37° C. for 96 hr, the polyethylene glycol derivative contained in the serum is recovered and GPC is measured to evaluate the degradation rate. The degradation rate is calculated from the peak area % of the GPC main fraction of the polyethylene glycol derivative before the stability test and the peak area % of the GPC main fraction of the polyethylene glycol derivative after the stability test. Specifically, the following formula is used.

degradation rate=(peak area % before test−peak area % after test)÷peak area % before test×100

For example, when the peak area % of the GPC main fraction of the degradable polyethylene glycol derivative before the stability test is 95% and the peak area % of the GPC main fraction after the stability test is 90%, the degradation rate is calculated as follows.

degradation rate=(95−90)÷95×100=5.26(%)

When the degradable polyethylene glycol derivative is degraded in blood, the desired half-life in blood cannot be achieved. Thus, in the stability test, the degradation rate after 96 hr is preferably not more than 10%, more preferably not more than 5%.

The test method for evaluating the intracellular degradability of the degradable polyethylene glycol derivative is not particularly limited. For example, a test including culturing cells in a medium containing a degradable polyethylene glycol derivative and the like can be mentioned. The cells and medium to be used here are not particularly limited. Specifically, a polyethylene glycol derivative is dissolved in RPMI-1640 medium to a concentration of 1-20 mg/mL, macrophage cells RAW264.7 are cultured in the medium at 37° C. for 96 hr, the polyethylene glycol derivative in the cells is recovered, and GPC is measured to evaluate the degradation rate. The degradation rate is calculated using the peak area % of the GPC main fraction of the polyethylene glycol derivative before and after the test, as in the stability test.

For example, when the peak area % of the GPC main fraction of the degradable polyethylene glycol derivative before the degradability test is 95% and the peak area % of the GPC main fraction after the test is 5%, the degradation rate is calculated as follows.

degradation rate=(95−5)÷95×100=94.7(%)

When the degradable polyethylene glycol derivative is not efficiently degraded in cells, the desired suppression of cell vacuoles cannot be achieved. Thus, in the degradability test, the degradation rate after 96 hr is preferably not less than 90%, more preferably not less than 95%.

The test method for evaluating the half-life in blood and distribution in vivo of the degradable polyethylene glycol derivative is not particularly limited. For example, a test including labeling with radioisotope or fluorescent substance, administering to mice or rats, followed by monitoring and the like can be mentioned.

A degradable peptide introduced into a polyethylene glycol derivative imparts intracellular degradability to polyethylene glycol. However, the peptide structure thereof may change the pharmacokinetics of polyethylene glycol. To confirm the effect of the introduced peptide structure on the pharmacokinetics, it is necessary to compare the blood half-life and distribution thereof in the body with those of a non-degradable polyethylene glycol derivative with the same molecular weight. Specifically, a radioisotope-labeled non-degradable polyethylene glycol derivative and a radioisotope-labeled degradable polyethylene glycol derivative are administered to mice, the radiation dose of blood and each organ is measured at plural time points, and quantification measurement can be performed.

The test method for evaluating suppression of cell vacuoles by a degradable polyethylene glycol derivative is not particularly limited. For example, as described in non-patent document 2, a test including continuing administration to mice or rats at high frequency and high dose for a long period of time and confirming images of the sections of organ and internal organ that are said to be susceptible to vacuole formation can be mentioned.

Specifically, a polyethylene glycol derivative is dissolved in saline to a concentration of 10-250 mg/mL, 20-100 μL thereof is continuously administered from the mouse tail vein 3 times per week for 4 weeks or longer, paraffin sections of cerebral choroid plexus, spleen, and the like that are organs said to be susceptible to vacuole formation are prepared and stained, and the images of the sections are confirmed by a pathological method to evaluate suppression of vacuoles.

In this evaluation, the dose of polyethylene glycol needs to be in large excess compared to the dose of polyethylene glycol that is generally used in the art.

Non-patent document 2 describes that vacuolization of cells by high-molecular-weight polyethylene glycol is related to accumulation of polyethylene glycol in tissue. The test method for evaluating accumulation of a degradable polyethylene glycol derivative in cells is not particularly limited, and evaluation can be made using section images prepared by the same method as the above-mentioned evaluation of vacuole. Stained section images of cerebral choroid plexus, spleen, and the like that are organs said to be susceptible to polyethylene glycol accumulation are confirmed by a pathological method, and accumulation of polyethylene glycol can be evaluated.

In this evaluation, the dose of polyethylene glycol needs to be in large excess compared to the dose of polyethylene glycol that is generally used in the art.

EXAMPLE $^1$H-NMR obtained in the following Examples was obtained from JNM-ECP400 or JNM-ECA600 manufactured by JEOL Datam Co., Ltd. A φ5 mm tube was used for the measurement, and $D_2O$ or $CDCl_3$ and $d_6$-DMSO containing tetramethylsilane (TMS) as an internal standard substance were used as deuterated solvents. The molecular weight and amine purity of the obtained polyethylene glycol derivative were calculated using liquid chromatography (GPC and HPLC). As a liquid chromatography system, "HLC-8320GPC EcoSEC" manufactured by Tosoh Corporation was used for GPC, and "ALLIANCE" manufactured by WATERS was used for HPLC. The analysis conditions of GPC and HPLC are shown below.

GPC Analysis (Molecular Weight Measurement)
  detector: differential refractometer
  column: ultrahydrogel 500 and ultrahydrogel 250 (manufactured by WATERS)
  mobile phase: 100 mM Acetate buffer+0.02% NaN$_3$ (pH 5.2)
  flow rate: 0.5 mL/min
  sample volume: 5 mg/mL, 20 μL
  column temperature: 30° C.

HPLC Analysis (Amine Purity Measurement)
  detector: differential refractometer
  column: TSKgel SP-5PW (manufactured by Tosoh Corporation)
  mobile phase: 1 mM Sodium phosphate buffer (pH 6.5)
  flow rate: 0.5 mL/min
  injection volume: 5 mg/mL, 20 μL
  column temperature: 40° C.

Example 1

Synthesis of Compound (p3)

(p3)

n = about 460

Example 1-1

Synthesis of Compound (p1)

(p1)

HO—(CH₂CH₂O)ₙ—CH₂CH₂CH₂—NH—C(=O)—CH₂—NH—C(=O)—CH(NH₂)—CH₂—C₆H₅ n = about 460

L-phenylalanyl-glycine with the N terminal protected by a 9-fluorenylmethyloxycarbonyl group (Fmoc group) (Fmoc-Phe-Gly) (400 mg) and "SUNBRIGHT HO-200PA" (15 g) having average molecular weight=20,000, manufactured by NOF CORPORATION were dissolved in acetonitrile (60 g) added thereto. Thereafter, diisopropylethylamine (233 mg) and 4-(4,6-dimethoxy-1,3,5-triazin-2-yl)-4-methylmorpholinium chloride n hydrate (DMT-MM) (311 mg) were added, and the mixture was reacted at room temperature under a nitrogen atmosphere for 1 hr. Thereafter, piperidine (639 mg) was added, and the mixture was reacted at room temperature under a nitrogen atmosphere for 2 hr. After completion of the reaction, the reaction mixture was diluted with toluene (500 g), hexane (300 g) was added, and the mixture was stirred at room temperature for 30 min. The resultant product was precipitated and suction filtered using 5A filter paper. The precipitate was recovered, dissolved again in toluene (300 g), hexane (150 g) was added, and the mixture was stirred at room temperature for 30 min. The resultant product was precipitated and suction filtered using 5A filter paper. The precipitate was recovered, washed with hexane (100 g) containing 2,6-di-tert-butyl-p-cresol (BHT) (20 mg), suction filtered using 5A filter paper, and dried in vacuo to give the above-mentioned compound (p1). yield 13 g.

$^1$H-NMR (d₆-DMSO): 1.73 ppm (m, 2H, —CO—NH—CH₂—$\underline{CH_2}$—CH₂—(O—CH₂—CH₂)n-OH), 2.59 ppm (dd, 1H, —NH—CO—CH—$\underline{CH_2}$—C₆H₅), 2.98 ppm (dd, 1H, —NH—CO—CH—$\underline{CH_2}$—C₆H₅), 3.10 ppm (q, 2H, —CO—NH—$\underline{CH_2}$—CH₂—CH₂—(O—CH₂—CH₂)n-OH), 3.48 ppm (m, about 1,900H, —CO—NH—CH₂—CH₂—CH₂—(O—$\underline{CH_2}$—$\underline{CH_2}$)n-OH), 7.24 ppm (m, 5H, —NH—CO—CH—CH₂—$\underline{C_6H_5}$), 7.73 ppm (t, 1H), 8.12 ppm (broad, 1H)

Example 1-2

Synthesis of Compound (p2)

(p2)

HO—(CH₂CH₂O)ₙ—CH₂CH₂CH₂—NH—C(=O)—CH₂—NH—C(=O)—CH(CH₂C₆H₅)—NH—C(=O)—(CH₂)₃—C(=O)—NH—CH(CH₂C₆H₅)—C(=O)—NH—CH₂—C(=O)—NH—CH₂CH₂CH₂—(OCH₂CH₂)ₙ—OH n = about 460

The compound (p1) (1.0 g) obtained in Example 1-1 and glutaric acid (3.2 mg) were dissolved in acetonitrile (4.0 g). Thereafter, diisopropylethylamine (8.4 mg) and DMT-MM (22 mg) were added, and the mixture was reacted at room temperature under a nitrogen atmosphere for 3 hr. After completion of the reaction, the reaction mixture was diluted with ethyl acetate (60 g), hexane (40 g) was added, and the mixture was stirred at room temperature for 15 min. The resultant product was precipitated and suction filtered using 5A filter paper. The precipitate was recovered, dissolved again in ethyl acetate (60 g), hexane (30 g) was added, and the mixture was stirred at room temperature for 30 min. The resultant product was precipitated and suction filtered using 5A filter paper. The precipitate was recovered, washed with hexane (30 g) containing BHT (6 mg), suction filtered using 5A filter paper, and dried in vacuo to give the above-mentioned compound (p2). yield 734 mg.

$^1$H-NMR ($d_6$-DMSO): 1.73 ppm (m, 4H, —CO—NH—CH$_2$—C$\underline{H_2}$—CH$_2$—(O—CH$_2$—CH$_2$)n-OH), 2.05 ppm (m, 6H, —NH—CO—C$\underline{H_2CH_2CH_2}$—CO—NH—), 2.59 ppm (dd, 2H, —NH—CO—CH—C$\underline{H_2}$—C$_6$H$_5$), 2.98 ppm (dd, 2H, —NH—CO—CH—C$\underline{H_2}$—$\underline{C_6H_5}$), 3.10 ppm (q, 4H, —CO—NH—C$\underline{H_2}$—CH$_2$—CH$_2$—(O—CH$_2$—CH$_2$)n-OH), 3.48 ppm (m, about 3,800H, —CO—NH—CH$_2$—CH$_2$—CH$_2$—(O—C$\underline{H_2}$—C$\underline{H_2}$)n-OH), 7.24 ppm (m, 10H, —NH—CO—CH—C$\underline{H_2}$—$\underline{C_6H_5}$), 7.73 ppm (t, 2H), 8.12 ppm (broad, 2H)

Example 1-3

Synthesis of Compound (p3)

The compound (p2) (500 mg) obtained in Example 1-2 was dissolved in dichloromethane (3.5 g). Thereafter, di(N-succinimidyl) carbonate (26 mg) and pyridine (10 mg) were added, and the mixture was reacted at room temperature under a under a nitrogen atmosphere for 8 hr. After completion of the reaction, the reaction mixture was washed with 5% brine (5 g), magnesium sulfate (100 mg) was added, and the mixture was stirred at room temperature for 30 min and suction filtered using 5A filter paper. The obtained filtrate was concentrated, and the concentrate was dissolved in ethyl acetate (30 g) containing BHT (6 mg). Hexane (15 g) was added and the mixture was stirred at room temperature for 30 min. The resultant product was precipitated and suction filtered using 5A filter paper. The precipitate was recovered, washed with hexane (30 g) containing BHT (6 mg), suction filtered using 5A filter paper, and dried in vacuo to give the above-mentioned compound (p3). yield 378 mg. The succinimidyl carbonation rate was 94% ($^1$H-NMR).

$^1$H-NMR ($d_6$-DMSO): 1.73 ppm (m, 4H, —CO—NH—CH$_2$—C$\underline{H_2}$—CH$_2$—O—(CH$_2$—CH$_2$—O)n-OCO-Succinimide), 2.05 ppm (m, 6H, —NH—CO—C$\underline{H_2}$—C$\underline{H_2}$—C$\underline{H_2}$—CO—NH—), 2.59 ppm (dd, 2H, —NH—CO—CH—C$\underline{H_2}$—$\underline{C_6H_5}$), 2.83 ppm (s, 8H, —CO—C$\underline{H_2}$—C$\underline{H_2}$—CO—), 2.98 ppm (dd, 2H, —NH—CO—CH—C$\underline{H_2}$—C$_6$H$_5$), 3.10 ppm (q, 4H, —CO—NH—C$\underline{H_2}$—CH$_2$—C$\underline{H_2}$—(O—CH$_2$—CH$_2$)n-OCO-Succinimide), 3.48 ppm (m, about 3,800H, —CO—NH—CH$_2$—CH$_2$—CH$_2$—(O—C$\underline{H_2}$—C$\underline{H_2}$)n-OCO-Succinimide), 7.24 ppm (m, 10H, —NH—CO—CH—CH$_2$—$\underline{C_6H_5}$), 7.73 ppm (t, 2H), 8.12 ppm (broad, 2H)

(p3)

n = about 460

Example 2

Synthesis of Compound (p8)

n = about 460 (p8)

Example 2-1

Synthesis of Compound (p4)

(p4)

n = about 460

"SUNBRIGHT DE-200PA" (20 g) having average molecular weight=20,000, manufactured by NOF CORPORATION was dissolved in toluene (80 g), di-tert-butyl dicarbonate (107 mg) was added, and the mixture was reacted at 40° C. under a nitrogen atmosphere for 3 hr. After completion of the reaction, toluene (100 g) was added, and the mixture was uniformly stirred. Hexane (100 g) was added and the mixture was stirred at room temperature for 30 min. The resultant product was precipitated, suction filtered using 5A filter paper, and the resultant product was vacuum dried. Thereafter, the resultant product was purified by ion exchange chromatography. To the recovered aqueous solution was added chloroform (500 g), and the mixture was stirred at room temperature for 30 min, and the resultant product was extracted into the organic layer. The obtained organic layer was dehydrated by adding sodium sulfate (10 g) and stirring the mixture at room temperature for 30 min, and then suction filtered using 5A filter paper. The obtained filtrate was concentrated, and the concentrate was redissolved in toluene (200 g), hexane (100 g) was added, and the mixture was stirred at room temperature for 30 min to allow for crystal precipitation. The crystals were suction filtered using 5A filter paper, and the precipitate was recovered and washed with hexane (100 g), suction filtered using 5A filter paper, and dried in vacuo to give the above-mentioned compound (p4). yield 9.1 g. HPLC: amine purity was 98%.

$^1$H-NMR (d$_6$-DMSO): 1.44 ppm (s, 9H, —CH$_2$—CH$_2$—CH$_2$—NH—CO—O—C(CH$_3$)$_3$), 1.64 ppm (m, 1H), 1.73 ppm (m, 4H), 2.68 ppm (t, 2H, —(CH$_2$—CH$_2$—O)n-CH$_2$—CH$_2$—CH$_2$—NH$_2$), 3.18 ppm (t, 2H, —CH$_2$—CH$_2$—CH$_2$—NH—CO—O—C(CH$_3$)$_3$), 3.35 ppm (m, 4H), 3.64 ppm (m, about 1,900H, —NH—CH$_2$—CH$_2$—CH$_2$—O—(CH$_2$—CH$_2$—O)n-), 6.76 ppm (broad, 1H)

Example 2-2

Synthesis of Compound (p5)

(p5)

n = about 460

L-glycyl-leucyl-phenylalanyl-glycine with the N terminal protected by a 9-fluorenylmethyloxycarbonyl group (Fmoc group) (Fmoc-Gly-Leu-Phe-Gly) (313 mg) and the compound (p4) (8.5 g) obtained in Example 2-1 were dissolved in acetonitrile (34 g) added thereto. Thereafter, diisopropylethylamine (132 mg) and DMT-MM (353 mg) were added, and the mixture was reacted at room temperature under a nitrogen atmosphere for 1 hr. Thereafter, piperidine (361 mg) was added, and the mixture was reacted at room temperature under a nitrogen atmosphere for 2 hr. After completion of the reaction, the reaction mixture was diluted with toluene (400 g), hexane (250 g) was added, and the mixture was stirred at room temperature for 30 min. The resultant product was precipitated and suction filtered using 5A filter paper. The precipitate was recovered, dissolved again in toluene (400 g), hexane (200 g) was added, and the mixture was stirred at room temperature for 30 min. The resultant product was precipitated and suction filtered using 5A filter paper. The precipitate was recovered, washed with hexane (200 g), suction filtered using 5A filter paper, and dried in vacuo to give the above-mentioned compound (p5). yield 7.6 g.

$^1$H-NMR (d$_6$-DMSO): 0.89 ppm (d, 3H, —NH—CO—CH—CH$_2$—CH(C$\underline{H}_3$)$_2$), 0.91 ppm (d, 3H, —NH—CO—CH—CH$_2$—CH(C$\underline{H}_3$)$_2$), 1.44 ppm (s, 9H, —CH$_2$—CH$_2$—CH$_2$—NH—CO—O—C(C$\underline{H}_3$)$_3$), 1.48 ppm (m, 1H, —NH—CO—C$\underline{H}$—CH$_2$—CH(CH$_3$)$_2$), 1.73 ppm (m, 6H), 2.68 ppm (t, 2H, —(CH$_2$—CH$_2$—O)n-CH$_2$—CH$_2$—C$\underline{H}_2$—NH$_2$), 3.18 ppm (t, 2H, —CH$_2$—CH$_2$—C$\underline{H}_2$—NH—CO—O—C(CH$_3$)$_3$), 3.35 ppm (m, 4H), 3.64 ppm (m, about 1,900H, —NH—CH$_2$—CH$_2$—CH$_2$—O—(C$\underline{H}_2$—C$\underline{H}_2$—O)n-), 4.09 ppm (s, 2H, —CH$_2$—CH$_2$—CH$_2$—NH—CO—C$\underline{H}_2$—NH—), 4.44 ppm (m, 1H), 4.92 ppm (m, 1H), 6.76 ppm (broad, 1H), 7.20 ppm (d, 2H, —NH—CO—CH—CH$_2$—C$\underline{6}$H$\underline{5}$), 7.32 ppm (m, 3H, —NH—CO—CH—CH$_2$—C$\underline{6}$H$\underline{5}$), 8.01 ppm (broad, 1H), 8.32 ppm (broad, 2H), 8.70 ppm (broad, 2H), 9.04 ppm (broad, 1H)

Example 2-3

Synthesis of Compound (p6)

n = about 460 (p6)

The compound (p5) (1.3 g) obtained in Example 2-2 and succinic acid (3.8 mg) were dissolved in acetonitrile (5.2 g). Thereafter, diisopropylethylamine (11 mg) and DMT-MM (29 mg) were added, and the mixture was reacted at room temperature under a nitrogen atmosphere for 3 hr. After completion of the reaction, the reaction mixture was diluted with ethyl acetate (100 g), hexane (60 g) was added, and the mixture was stirred at room temperature for 15 min. The resultant product was precipitated and suction filtered using 5A filter paper. The precipitate was recovered, dissolved in ethyl acetate (100 g) containing BHT (20 mg), hexane (50 g) was added, and the mixture was stirred at room temperature for 30 min. The resultant product was precipitated and suction filtered using 5A filter paper. The precipitate was recovered, washed with hexane (50 g) containing BHT (10 mg), suction filtered using 5A filter paper, and dried in vacuo to give the above-mentioned compound (p6). yield 889 mg.

$^1$H-NMR (d$_6$-DMSO): 0.89 ppm (d, 6H, —NH—CO—CH—CH$_2$—CH(CH$_3$)$_2$), 0.91 ppm (d, 6H, —NH—CO—CH—CH$_2$—CH(CH$_3$)$_2$), 1.44 ppm (s, 18H, —CH$_2$—CH$_2$—CH$_2$—NH—CO—O—C(CH$_3$)$_3$), 1.48 ppm (m, 2H, —NH—CO—CH—CH$_2$—CH(CH$_3$)$_2$), 1.73 ppm (m, 12H), 2.34 ppm (m, 4H), 2.68 ppm (t, 4H, —(CH$_2$—CH$_2$—O)n-CH$_2$—CH$_2$—CH$_2$—), 3.18 ppm (t, 4H, —CH$_2$—CH$_2$—CH$_2$—NH—CO—O—C(CH$_3$)$_3$), 3.35 ppm (m, 8H), 3.64 ppm (m, about 3,800H, —NH—CH$_2$—CH$_2$—CH$_2$—O—(CH$_2$—CH$_2$—O)n-), 4.09 ppm (s, 12H), 4.44 ppm (m, 2H), 4.92 ppm (m, 2H), 6.76 ppm (broad, 1H), 7.20 ppm (d, 4H, —NH—CO—CH—CH$_2$—C$_6$H$_5$), 7.32 ppm (m, 6H, —NH—CO—CH—CH$_2$—C$_6$H$_5$), 8.01 ppm (broad, 2H), 8.32 ppm (broad, 4H), 9.04 ppm (broad, 4H)

Example 2-4

Synthesis of Compound (p7)

The compound (p6) (800 mg) obtained in Example 2-3 was dissolved in ion exchange water (3.3 g), 6N hydrochloric acid (0.7 g) was added, and the mixture was reacted at room temperature under a nitrogen atmosphere for 3 hr. After completion of the reaction, 1N aqueous sodium hydroxide solution was added to adjust the pH to 6.5, and sodium chloride (1.0 g) was added to dissolve same. To the obtained solution was added 1N aqueous sodium hydroxide solution to adjust the pH to 7.10, chloroform (10 g) containing BHT (2 mg) was added, and the mixture was stirred at room temperature for 20 min. The resultant product was extracted into the organic layer. The organic layer and the aqueous layer were separated, the organic layer was recovered, chloroform (10 g) containing BHT (2 mg) was added again to the aqueous layer, and the mixture was stirred at room temperature for 20 min. The resultant product was extracted into the organic layer. The organic layers obtained by the first extraction and the second extraction were combined and concentrated at 40° C. The obtained concentrate was dissolved in toluene (50 g), sodium sulfate (1.0 g) was added, and the mixture was dehydrated by stirring at room temperature for 30 min. Thereafter, the mixture was suction filtered using 5A filter paper. Hexane (30 g) was added to the filtrate, and the mixture was stirred at room temperature for 30 min. The resultant product was precipitated and suction filtered using 5A filter paper. The precipitate was recovered, washed with hexane (30 g) containing BHT (6 mg), suction filtered using 5A filter paper, and dried in vacuo to give the above-mentioned compound (p7). yield 675 mg. HPLC: amine purity was 91%.

$^1$H-NMR (d$_6$-DMSO): 0.89 ppm (d, 6H, —NH—CO—CH—CH$_2$—CH(CH$_3$)$_2$), 0.91 ppm (d, 6H, —NH—CO—CH—CH$_2$—CH(CH$_3$)$_2$), 1.48 ppm (m, 2H, —NH—CO—CH—CH$_2$—CH(CH$_3$)$_2$), 1.73 ppm (m, 12H), 2.34 ppm (m, 4H), 2.68 ppm (t, 4H, —(CH$_2$—CH$_2$—O)n-CH$_2$—CH$_2$—CH$_2$—), 3.18 ppm (t, 4H, —CH$_2$—CH$_2$—CH$_2$—NH—CO—O—C(CH$_3$)$_3$), 3.35 ppm (m, 8H), 3.64 ppm (m, about 3,800H, —NH—CH$_2$—CH$_2$—CH$_2$—(O—CH$_2$—CH$_2$)n-), 4.09 ppm (s, 12H), 4.44 ppm (m, 2H), 4.92 ppm (m, 2H), 6.76 ppm (broad, 1H), 7.20 ppm (d, 4H, —NH—CO—CH—CH$_2$—C$_6$H$_5$), 7.32 ppm (m, 6H, —NH—CO—CH—CH$_2$—C$_6$H$_5$), 8.01 ppm (broad, 2H), 8.32 ppm (broad, 4H), 9.04 ppm (broad, 4H)

n = about 460 (p7)

Example 2-5

Synthesis of Compound (p8)

[Chemical structure of compound p8, showing a maleimide group connected via CH₂CH₂-C(O)-NH-CH₂CH₂CH₂-O-(CH₂CH₂O)ₙ-CH₂CH₂CH₂-NH-Gly-Leu-Phe-Gly-NH-C(O)-(CH₂)₂-C(O)- linker to another symmetric half ending in a maleimide group]

n = about 460 (p8)

The compound (p7) (400 mg) obtained in Example 2-4 was dissolved in acetonitrile (320 mg) and toluene (2.1 g). Thereafter, N-methylmorpholine (10 mg) and N-succinimidyl 3-maleimidopropionate (27 mg) were added, and the mixture was reacted at room temperature under a nitrogen atmosphere and shading for 6 hr. After completion of the reaction, the reaction mixture was diluted with ethyl acetate (50 g) containing BHT (10 mg), hexane (30 g) was added, and the mixture was stirred at room temperature for 15 min. The resultant product was precipitated and suction filtered using 5A filter paper. The precipitate was recovered, washed with hexane (30 g) containing BHT (6 mg), suction filtered using 5A filter paper, and dried in vacuo to give the above-mentioned compound (p8). yield 227 mg. The maleimidation rate was 96% ($^1$H-NMR).

$^1$H-NMR ($d_6$-DMSO): 0.89 ppm (d, 6H, —NH—CO—CH—CH$_2$—CH($\underline{CH_3}$)$_2$), 0.91 ppm (d, 6H, —NH—CO—CH—CH$_2$—CH($\underline{CH_3}$)$_2$), 1.48 ppm (m, 2H, —NH—CO—$\underline{CH}$—CH$_2$—CH($\overline{CH_3}$)$_2$), 1.73 ppm (m, 12H), 2.34 ppm (m, $\overline{4H}$), 2.68 ppm (t, 4H, —(CH$_2$—CH$_2$—O)n-CH$_2$—CH$_2$—$\underline{CH_2}$—), 3.18 ppm (t, 4H, —CH$_2$—CH$_2$—$\underline{CH_2}$—NH—CO—O—C(CH$_3$)$_3$), 3.35 ppm (m, 8H), 3.64 ppm (m, about 3,800H, —NH—CH$_2$—CH$_2$—CH$_2$—O—($\underline{CH_2—CH_2}$—O)n-), 4.09 ppm (s, 12H), 4.44 ppm (m, 2H), 4.76 ppm (m, 4H, —NH—CO—CH$_2$—$\underline{CH_2}$-Maleimide), 4.92 ppm (m, 2H), 6.76 ppm (broad, 1H), 6.68 ppm (s, 4H, —CH$_2$—CH$_2$—CH$_2$—NH—CO—CH$_2$—CH$_2$—$\underline{C_4NO_2H_2}$), 7.20 ppm (d, 4H, —NH—CO—CH—CH$_2$—$\underline{C_6H_5}$), 7.32 ppm (m, 6H, —NH—CO—CH—CH$_2$—$\underline{C_6H_5}$), 8.01 ppm (broad, 2H), 8.32 ppm (broad, 4H), 9.04 ppm (broad, 4H)

Example 3

Synthesis of Compound (p13)

[Chemical structure of compound p13, showing N-hydroxysuccinimide carbonate-O-(CH$_2$CH$_2$O)$_n$-CH$_2$CH$_2$CH$_2$-NH-Gly-Phe-NH-C(O)-(CH$_2$)$_3$-C(O)- linker]

n = about 460 (p13)

Example 3-1

Synthesis of Compound (p9)

(p9)

n = about 460

The compound (p1) (2.0 g) obtained in Example 1-1, sodium acetate (82 mg), and glutaric anhydride (132 mg) were dissolved in toluene (6.0 g), and the mixture was reacted under a nitrogen atmosphere at 40° C. for 7 hr. After completion of the reaction, the mixture was diluted with ethyl acetate (100 g), suction filtered using 5A filter paper, hexane (50 g) was added to the obtained filtrate and the mixture was stirred at room temperature for 15 min. The resultant product was precipitated and suction filtered using 5A filter paper. The precipitate was recovered. The obtained precipitate was dissolved in ethyl acetate (100 g), hexane (50 g) was added, and the mixture was stirred at room temperature for 30 min, and the resultant product was precipitated. The precipitate was suction filtered using 5A filter paper, recovered, washed with hexane (50 g), suction filtered using 5A filter paper, and dried in vacuo to give the above-mentioned compound (p9). yield 1.8 g.

$^1$H-NMR ($d_6$-DMSO): 1.73 ppm (m, 2H, —CO—NH—CH$_2$—CH$_2$—CH$_2$—(O—CH$_2$—CH$_2$)n-OH), 2.05 ppm (m, 4H, —NH—CO—CH$_2$—CH$_2$—CH$_2$—COOH), 2.30 ppm (t, 2H, —NH—CO—CH$_2$—CH$_2$—CH$_2$—COOH), 2.59 ppm (dd, 1H, —NH—CO—CH—CH$_2$—C$_6$H$_5$), 2.98 ppm (dd, 1H, —NH—CO—CH—CH$_2$—C$_6$H$_5$), 3.10 ppm (q, 2H, —CO—NH—CH$_2$—CH$_2$—CH$_2$—(O—CH$_2$—CH$_2$)n-OH), 3.48 ppm (m, about 1,900H, —CO—NH—CH$_2$—CH$_2$—CH$_2$—(O—CH$_2$—CH$_2$)n-OH), 7.24 ppm (m, 5H, —NH—CO—CH—CH$_2$—C$_6$H$_5$), 8.12 ppm (broad, 1H), 9.04 ppm (broad, 1H)

Example 3-2

Synthesis of Compound (p10)

(p10)

n = about 460

The compound (p9) (1.6 g) obtained in Example 3-1 and compound (p5) (1.6 g) obtained in Example 2-2 were dissolved in acetonitrile (10 g). Thereafter, diisopropylethylamine (25 mg) and DMT-MM (66 mg) were added, and the mixture was reacted at room temperature under a nitrogen atmosphere for 3 hr. After completion of the reaction, the reaction mixture was diluted with ethyl acetate (150 g), hexane (80 g) was added, and the mixture was stirred at room temperature for 15 min. The resultant product was precipitated and suction filtered using 5A filter paper. The precipitate was recovered, dissolved again in ethyl acetate (100 g), hexane (50 g) was added, and the mixture was stirred at room temperature for 15 min. The resultant product was precipitated and suction filtered using 5A filter paper. The precipitate was recovered, washed with hexane (80 g) containing BHT (16 mg), suction filtered using 5A filter paper, and dried in vacuo to give the above-mentioned compound (p10). yield 2.6 g.

$^1$H-NMR (d$_6$-DMSO): 0.89 ppm (d, 3H, —NH—CO—CH$_2$—CH$_2$—CH(CH$_3$)$_2$), 0.91 ppm (d, 3H, —NH—CO—CH$_2$—CH$_2$—CH(CH$_3$)$_2$), 1.44 ppm (s, 9H, —CH$_2$—CH$_2$—CH$_2$—NH—CO—O—C(CH$_3$)$_3$), 1.48 ppm (m, 1H, —NH—CO—CH—CH$_2$—CH(CH$_3$)$_2$), 1.73 ppm (m, 8H), 2.05 ppm (m, 4H, —NH—CO—CH$_2$—CH$_2$—CH$_2$—CO—NH—), 2.30 ppm (t, 2H, —NH—CO—CH$_2$—CH$_2$—CH$_2$—CO—NH—), 2.59 ppm (dd, 1H, —NH—CO—CH—CH$_2$—C$_6$H$_5$), 2.98 ppm (dd, 1H, —NH—CO—CH—CH$_2$—C$_6$H$_5$), 3.10 ppm (m, 10H), 3.48 ppm (m, about 3,800H, —CO—NH—CH$_2$—CH$_2$—CH$_2$—(O—CH$_2$—CH$_2$)n-), 4.09 ppm (s, 6H), 6.76 ppm (broad, 1H), 7.24 ppm (m, 10H, —NH—CO—CH—CH$_2$—C$_6$H$_5$), 8.12 ppm (broad, 2H), 8.32 ppm (broad, 3H), 9.04 ppm (broad, 3H)

Example 3-3

Synthesis of Compound (p11)

(p11)

n = about 460

The compound (p10) (2.3 g) obtained in Example 3-2 was dissolved in ion exchange water (9.4 g), 6N hydrochloric acid (2.1 g) was added, and the mixture was reacted at room temperature under a nitrogen atmosphere for 3 hr. After completion of the reaction, 1N aqueous sodium hydroxide solution was added to adjust to pH 6.5, and sodium chloride (2.5 g) was added and dissolved therein. To the obtained solution was added 1N aqueous sodium hydroxide solution to adjust the pH to 7.10, chloroform (20 g) containing BHT (4 mg) was added and the mixture was stirred at room temperature for 20 min. The resultant product was extracted into the organic layer. The organic layer and the aqueous layer were separated, the organic layer was recovered, chloroform (20 g) containing BHT (4 mg) was added again to the aqueous layer, and the mixture was stirred at room temperature for 20 min. The resultant product was extracted into the organic layer. The organic layers obtained by the first extraction and the second extraction were combined and concentrated at 40° C., the obtained concentrate was dissolved in toluene (150 g), sodium sulfate (5.0 g) was added, and the mixture was stirred at room temperature for 30 min, and suction filtered using 5A filter paper. Hexane (80 g) was added to the filtrate and the mixture was stirred at room temperature for 30 min. The resultant product was precipitated and suction filtered using 5A filter paper. The precipitate was recovered, washed with hexane (50 g) containing BHT (10 mg), suction filtered using 5A filter paper, and dried in vacuo to give the above-mentioned compound (p11). yield 1.7 g. HPLC: the amine purity was 90%.

$^1$H-NMR (d$_6$-DMSO): 0.89 ppm (d, 3H, —NH—CO—CH$_2$—CH$_2$—CH(CH$_3$)$_2$), 0.91 ppm (d, 3H, —NH—CO—CH$_2$—CH$_2$—CH(CH$_3$)$_2$), 1.48 ppm (m, 1H, —NH—CO—CH—CH$_2$—CH(CH$_3$)$_2$), 1.73 ppm (m, 8H), 2.05 ppm (m, 4H, —NH—CO—CH$_2$—CH$_2$—CH$_2$—CO—NH—), 2.30 ppm (t, 2H, —NH—CO—CH$_2$—CH$_2$—CH$_2$—CO—NH—), 2.59 ppm (dd, 2H, —NH—CO—CH—CH$_2$—C$_6$H$_5$), 2.68 ppm (t, 2H, NH$_2$—CH$_2$—CH$_2$—CH$_2$—(O—CH$_2$—CH$_2$)n-), 2.98 ppm (dd, 2H, —NH—CO—CH—CH$_2$—C$_6$H$_5$), 3.48 ppm (m, about 3,800H, —CO—NH—CH$_2$—CH$_2$—CH$_2$—(O—CH$_2$—CH$_2$)n-), 4.09 ppm (s, 6H), 7.24 ppm (m, 10H, —NH—CO—CH—CH$_2$—C$_6$H$_5$), 8.12 ppm (broad, 2H), 8.32 ppm (broad, 3H), 9.04 ppm (broad, 3H)

Example 3-4

Synthesis of Compound (p12)

(p12)

n = about 460

The compound (p11) (1.5 g) obtained in Example 3-3 was dissolved in acetonitrile (1.2 g) and toluene (7.8 g). Thereafter, N-methylmorpholine (19 mg) and N-succinimidyl 3-maleimidopropionate (21 mg) were added, and the mixture was reacted at room temperature under a nitrogen atmosphere and shading for 3 hr. After completion of the reaction, the reaction mixture was diluted with ethyl acetate (50 g) containing BHT (10 mg), hexane (30 g) was added, and the mixture was stirred at room temperature for 15 min. The resultant product was precipitated and suction filtered using 5A filter paper. The precipitate was recovered, washed with hexane (20 g) containing BHT (4 mg), suction filtered using 5A filter paper, and dried in vacuo to give the above-mentioned compound (p12). yield 1.3 g. The maleimidation rate was 92% ($^1$H-NMR).

$^1$H-NMR ($d_6$-DMSO): 0.89 ppm (d, 3H, —NH—CO—CH$_2$—CH$_2$—CH(CH$_3$)$_2$), 0.91 ppm (d, 3H, —NH—CO—CH$_2$—CH$_2$—CH(CH$_3$)$_2$), 1.48 ppm (m, 1H, —NH—CO—CH—CH$_2$—CH(CH$_3$)$_2$), 1.73 ppm (m, 8H), 2.05 ppm (m, 4H, —NH—CO—CH$_2$—CH$_2$—CH$_2$—CO—NH—), 2.30 ppm (t, 2H, —NH—CO—CH$_2$—CH$_2$—CH$_2$—CO—NH—), 2.59 ppm (dd, 2H, —NH—CO—CH—CH$_2$—C$_6$H$_5$), 2.68 ppm (t, 2H, C$_4$NO$_2$H$_2$—CH$_2$—CH$_2$—CO—NH—CH$_2$—CH$_2$—CH$_2$—O—(CH$_2$—CH$_2$—O)n-), 2.98 ppm (dd, 2H, —NH—CO—CH—CH$_2$—C$_6$H$_5$), 3.48 ppm (m, about 3,800H, —CO—NH—CH$_2$—CH$_2$—CH$_2$—O—(CH$_2$—CH$_2$—O)n-), 4.09 ppm (s, 6H), 6.68 ppm (s, 2H, —NH—CO—CH$_2$—CH$_2$—C$_4$NO$_2$H$_2$), 7.24 ppm (m, 10H, —NH—CO—CH—CH$_2$—C$_6$H$_5$), 8.12 ppm (broad, 3H), 8.32 ppm (broad, 3H), 9.04 ppm (broad, 3H)

Example 3-5

Synthesis of Compound (p13)

(p13)

n = about 460

The compound (p12) (800 mg) obtained in Example 3-4 was dissolved in dichloromethane (5.6 g). Thereafter, di(N-succinimidyl) carbonate (20 mg) and pyridine (8 mg) were added, and the mixture was reacted at room temperature under a nitrogen atmosphere for 8 hr. After completion of the reaction, the reaction mixture was washed with 5% brine (5 g), magnesium sulfate (100 mg) was added, and the mixture was stirred at 25° C. for 30 min, and suction filtered using 5A filter paper. The obtained filtrate was concentrated, and the concentrate was dissolved in toluene (100 g) added thereto, hexane (50 g) was added, and the mixture was stirred at room temperature for 15 min. The resultant product was precipitated and suction filtered using 5A filter paper. The precipitate was recovered, washed with hexane (50 g) containing BHT (10 mg), suction filtered using 5A filter paper, and dried in vacuo to give the above-mentioned compound (p13). yield 653 mg. The succinimidyl carbonation rate was 93% ($^1$H-NMR).

$^1$H-NMR (d$_6$-DMSO): 0.89 ppm (d, 3H, —NH—CO—CH$_2$—CH$_2$—CH(CH$_3$)$_2$), 0.91 ppm (d, 3H, —NH—CO—CH$_2$—CH$_2$—CH(CH$_3$)$_2$), 1.48 ppm (m, 1H, —NH—CO—CH—CH$_2$—CH(CH$_3$)$_2$), 1.73 ppm (m, 8H), 2.05 ppm (m, 4H, —NH—CO—CH$_2$—CH$_2$—CH$_2$—CO—NH—), 2.30 ppm (t, 2H, —NH—CO—CH$_2$—CH$_2$—CH$_2$—CO—NH—), 2.59 ppm (dd, 2H, —NH—CO—CH—CH$_2$—C$_6$H$_5$), 2.68 ppm (t, 2H, C$_4$NO$_2$H$_2$—CH$_2$—CH$_2$—CO—NH—CH$_2$—CH$_2$—CH$_2$—O—(CH$_2$—CH$_2$—O)n-), 2.83 ppm (s, 4H, —CO—CH$_2$—CH$_2$—CO—), 2.98 ppm (dd, 2H, —NH—CO—CH—CH$_2$—C$_6$H$_5$), 3.48 ppm (m, about 3,800H, —CO—NH—CH$_2$—CH$_2$—CH$_2$—O—(CH$_2$—CH$_2$—O)n-), 4.09 ppm (s, 6H), 6.68 ppm (s, 2H, —NH—CO—CH$_2$—CH$_2$—C$_4$NO$_2$H$_2$), 7.24 ppm (m, 10H, —NH—CO—CH—CH$_2$—C$_6$H$_5$), 8.12 ppm (broad, 3H), 8.32 ppm (broad, 3H), 9.04 ppm (broad, 3H)

Example 4

Synthesis of Compound (p17)

(p17)

n = about 230

Example 4-1

Synthesis of Compound (p14)

(p14)

HO—(CH₂CH₂O)ₙ—CH₂CH₂CH₂—NH—C(O)—CH₂—NH—C(O)—CH(NH₂)—CH₂—C₆H₅ n = about 230

By the same production method as in Example 1-1, and using L-phenylalanyl-glycine with the N terminal protected by a 9-fluorenylmethyloxycarbonyl group (Fmoc group) (Fmoc-Phe-Gly) (400 mg) and "SUNBRIGHT HO-100PA" (7.5 g) having average molecular weight=10,000, manufactured by NOF CORPORATION as starting materials, the above-mentioned compound (p14) was obtained. yield 6.5 g. HPLC: the amine purity was 98%.

$^1$H-NMR (d$_6$-DMSO): 1.73 ppm (m, 2H, —CO—NH—CH₂—CH₂—CH₂—(O—CH₂—CH₂)n-OH), 2.59 ppm (dd, 1H, —NH—CO—CH—CH₂—C₆H₅), 2.98 ppm (dd, 1H, —NH—CO—CH—CH₂—C₆H₅), 3.10 ppm (q, 2H, —CO—NH—CH₂—CH₂—CH₂—(O—CH₂—CH₂)n-OH), 3.48 ppm (m, about 950H, —CO—NH—CH₂—CH₂—CH₂—(O—CH₂—CH₂)n-OH), 7.24 ppm (m, 5H, —NH—CO—CH—CH₂—C₆H₅), 7.73 ppm (t, 1H), 8.12 ppm (broad, 1H)

Example 4-2

Synthesis of Compound (p15)

(p15)

n = about 230

L-glutamic acid with the N terminal protected by a 9-fluorenylmethyloxycarbonyl group (Fmoc group) (Fmoc-Glu-OH) (93 mg) and the compound (p14) (5.5 g) obtained in Example 4-1 were dissolved by heating at 30° C. in acetonitrile (24 g) added thereto. Thereafter, diisopropylethylamine (86 mg) and DMT-MM (232 mg) were added, and the mixture was reacted at room temperature under a nitrogen atmosphere for 1 hr. Thereafter, piperidine (1.1 g) was added, and the mixture was reacted at room temperature under a nitrogen atmosphere for 2 hr. After completion of the reaction, the reaction mixture was diluted with toluene (150 g), hexane (80 g) was added, and the mixture was stirred at room temperature for 15 min. The resultant product was precipitated and suction filtered using 5A filter paper. The precipitate was recovered, dissolved again in toluene (150 g), hexane (80 g) was added, and the mixture was stirred at room temperature for 15 min. The resultant product was precipitated and suction filtered using 5A filter paper. The precipitate was recovered, washed with hexane (50 g) containing BHT (10 mg), suction filtered using 5A filter paper, and dried in vacuo to give the above-mentioned compound (p15). yield 4.6 g. HPLC: amine purity was 92%.

$^1$H-NMR (d$_6$-DMSO): 1.54 ppm (m, 2H, —NH—CO—CH(NH₂)—CH₂—CH₂—), 1.62 ppm (m, 4H, —CO—NH—CH₂—CH₂—CH₂—), 1.97 ppm (m, 2H, —NH—CO—CH(NH₂)—CH₂—CH₂—), 2.74 ppm (dd, 2H, —CO—NH—CH—CH₂—C₆H₅), 2.81 ppm (dd, 2H, —CO—NH—CH—CH₂—C₆H₅), 3.11 ppm (m, 11H), 3.64 ppm (m, about 1,900H, —CO—NH—CH₂—CH₂—CH₂—(O—CH₂—CH₂)n-OH), 4.49 ppm (m, 4H, —CO—NH—CH—CH₂—C₆H₅), 4.57 ppm (m, 2H, —CO—NH—CH—CH₂—C₆H₅), 7.25 ppm (m, 10H, —CO—NH—CH—CH₂—C₆H₅), 7.74 ppm (m, 2H), 8.44 ppm (m, 2H), 8.61 ppm (m, 2H)

Example 4-3

Synthesis of Compound (p16)

(p16)

[Chemical structure diagram]

n = about 230

The compound (p15) (1.0 g) obtained in Example 4-2 and glutaric acid (3.3 mg) were dissolved in acetonitrile (8.0 g). Thereafter, diisopropylethylamine (8.4 mg) and DMT-MM (22.6 mg) were added, and the mixture was reacted at room temperature under a nitrogen atmosphere for 3 hr. After completion of the reaction, the reaction mixture was diluted with toluene (100 g), hexane (60 g) was added, and the mixture was stirred at room temperature for 15 min. The resultant product was precipitated and suction filtered using 5A filter paper. The precipitate was recovered, dissolved again in toluene (100 g), hexane (50 g) was added, and the mixture was stirred at room temperature for 15 min. The resultant product was precipitated and suction filtered using 5A filter paper. The precipitate was recovered, washed with hexane (50 g) containing BHT (10 mg), suction filtered using 5A filter paper, and dried in vacuo to give the above-mentioned compound (p16). yield 683 mg.

$^1$H-NMR ($d_6$-DMSO): 1.54 ppm (m, 4H, —NH—CO—CH(NH)—$\underline{CH_2}$—CH$_2$—), 1.62 ppm (m, 8H), 1.97 ppm (m, 4H, —NH—CO—CH(NH)—CH$_2$—$\underline{CH_2}$—), 2.05 ppm (m, 4H, —NH—CO—$\underline{CH_2}$—CH$_2$—CH$_2$—CO—NH—), 2.30 ppm (t, 2H, —NH—CO—CH$_2$—CH$_2$—$\underline{CH_2}$—CO—NH—), 2.74 ppm (dd, 2H, —CO—NH—CH—$\underline{CH_2}$—C$_6$H$_5$), 2.81 ppm (dd, 2H, —CO—NH—CH—$\underline{CH_2}$—C$_6$H$_5$), 3.11 ppm (m, 22H), 3.64 ppm (m, about 3,800H, —CO—NH—CH$_2$—CH$_2$—CH$_2$—(O—$\underline{CH_2}$—$\underline{CH_2}$)n-OH), 4.49 ppm (m, 8H, —CO—NH—CH—$\underline{CH_2}$—C$_6$H$_5$), 4.57 ppm (m, 4H, —CO—NH—$\underline{CH}$—CH$_2$—C$_6$H$_5$), 7.25 ppm (m, 20H, —CO—NH—CH—CH$_2$—$\underline{C_6H_5}$), 7.74 ppm (m, 4H), 8.44 ppm (m, 4H), 8.61 ppm (m, 4H)

Example 4-4

Synthesis of Compound (p17)

(p17)

[Chemical structure diagram]

n = about 230

The compound (p16) (500 mg) obtained in Example 4-3 was dissolved by heating at 30° C. in toluene (10 g), and azeotropically dehydrated under reduced pressure. Thereafter, the concentrate was dissolved in chloroform (3.0 g), N-hydroxyphthalimide (7.2 mg), triphenylphosphine (36 mg), and diisopropyl azodicarboxylate (24 mg) were added, and the mixture was reacted at room temperature under a nitrogen atmosphere for 4 hr. After completion of the reaction, methanol (10 mg) was added to the reaction mixture and the mixture was stirred at 25° C. for 30 min, ethylenediamine monohydrate (20 mg) was added, and the mixture was reacted at 40° C. under a nitrogen atmosphere for 1 hr. After completion of the reaction, the reaction mixture was diluted with toluene (50 g), hexane (30 g) was added, and the mixture was stirred at room temperature for 30 min. The resultant product was precipitated and suction filtered using 5A filter paper. The precipitate was recovered, washed with hexane (20 g) containing BHT (4 mg), suction filtered using 5A filter paper, and dried in vacuo to give the above-mentioned compound (p17). yield 263 mg. HPLC: The oxyamine purity was 90%.

$^1$H-NMR ($d_6$-DMSO): 1.54 ppm (m, 4H, —NH—CO—CH(NH)—$\underline{CH_2}$—$CH_2$—), 1.62 ppm (m, 8H), 1.97 ppm (m, 4H, —NH—CO—CH(NH)—$CH_2$—$\underline{CH_2}$—), 2.05 ppm (m, 4H, —NH—CO—$\underline{CH_2}$—$CH_2$—$CH_2$—CO—NH—), 2.30 ppm (t, 2H, —NH—CO—$CH_2$—$CH_2$—$\underline{CH_2}$—CO—NH—), 2.74 ppm (dd, 2H, —CO—NH—CH—$\underline{CH_2}$—$C_6H_5$), 2.81 ppm (dd, 2H, —CO—NH—CH—$\underline{CH_2}$—$C_6H_5$), 3.11 ppm (m, 22H), 3.64 ppm (m, about 3,800H, —CO—NH—$CH_2$—$CH_2$—$CH_2$—(O—$\underline{CH_2}$—$\underline{CH_2}$)n-$ONH_2$), 4.49 ppm (m, 8H, —CO—NH—CH—$\underline{CH_2}$—$C_6H_5$), 4.57 ppm (m, 4H, —CO—NH—$\underline{CH}$—$CH_2$—$C_6H_5$), 7.25 ppm (m, 20H, —CO—NH—CH—$CH_2$—$\underline{C_6H_5}$), 7.74 ppm (m, 4H), 8.44 ppm (m, 4H), 8.61 ppm (m, 4H)

Example 5

Synthesis of Compound (p23)

(p23)

n = about 460

Example 5-1

Synthesis of Compound (p18)

(p18)

n = about 460

L-glutamic acid with the N terminal protected by a 9-fluorenylmethyloxycarbonyl group (Fmoc group) (Fmoc-Glu-OH) (18 mg) and the compound (p5) (4.0 g) obtained in Example 2-2 were dissolved by heating at 30° C. in acetonitrile (16 g) added thereto. Thereafter, diisopropylethylamine (17 mg) and DMT-MM (36 mg) were added, and the mixture was reacted at room temperature under a nitrogen atmosphere for 1 hr. Thereafter, piperidine (212 mg) was added, and the mixture was reacted at room temperature under a nitrogen atmosphere for 2 hr. After completion of the reaction, the reaction mixture was diluted with toluene (150 g), hexane (90 g) was added, and the mixture was stirred at room temperature for 30 min. The resultant product was precipitated and suction filtered using 5A filter paper. The precipitate was recovered, dissolved in toluene (200 g) containing BHT (40 mg), hexane (100 g) was added, and the mixture was stirred at room temperature for 30 min. The resultant product was precipitated and suction filtered using 5A filter paper. The precipitate was recovered, washed with hexane (150 g) containing BHT (30 mg), suction filtered using 5A filter paper, and dried in vacuo to give the above-mentioned compound (p18). yield 2.7 g. HPLC: The amine purity was 91%.

$^1$H-NMR (d$_6$-DMSO): 0.89 ppm (d, 6H, —NH—CO—CH—CH$_2$—CH(CH$_3$)$_2$), 0.91 ppm (d, 6H, —NH—CO—CH—CH$_2$—CH(CH$_3$)$_2$), 1.44 ppm (s, 18H, —CH$_2$—CH$_2$—CH$_2$—NH—CO—O—C(CH$_3$)$_3$), 1.48 ppm (m, 2H, —NH—CO—CH—CH$_2$—CH(CH$_3$)$_2$), 1.73 ppm (m, 12H), 2.05 ppm (m, 4H), 3.18 ppm (t, 4H, —CH$_2$—CH$_2$—CH$_2$—NH—CO—O—C(CH$_3$)$_3$), 3.64 ppm (m, about 3,800H, —NH—CH$_2$—CH$_2$—O—(CH$_2$—CH$_2$—O)n-), 4.09 ppm (s, 8H), 4.44 ppm (m, 2H), 4.92 ppm (m, 2H), 6.76 ppm (broad, 2H), 7.25 ppm (m, 20H, —CO—NH—CH—CH$_2$—C$_6$H$_5$), 8.01 ppm (broad, 2H), 8.32 ppm (broad, 4H), 8.70 ppm (broad, 2H), 9.04 ppm (broad, 4H)

Example 5-2

Synthesis of Compound (p19)

(p19)

n = about 460

By the same production method as in Example 4-2, and using L-glutamic acid with the N terminal protected by a 9-fluorenylmethyloxycarbonyl group (Fmoc group) (Fmoc-Glu-OH) (18 mg) and the compound (p1) (4.0 g) obtained in Example 1-1 as starting materials, the above-mentioned compound (p19) was obtained. yield 3.2 g. HPLC: The amine purity was 90%.

$^1$H-NMR (d$_6$-DMSO): 1.54 ppm (m, 2H, —NH—CO—CH(NH$_2$)—CH$_2$—CH$_2$—), 1.62 ppm (m, 4H, —CO—NH—CH$_2$—CH$_2$—CH$_2$—), 1.97 ppm (m, 2H, —NH—CO—CH(NH$_2$)—CH$_2$—CH$_2$—), 2.74 ppm (dd, 2H, —CO—NH—CH—CH$_2$—C$_6$H$_5$), 2.81 ppm (dd, 2H, —CO—NH—CH—CH$_2$—C$_6$H$_5$), 3.11 ppm (m, 11H), 3.64 ppm (m, about 1,900H, —CO—NH—CH$_2$—CH$_2$—CH$_2$—(O—CH$_2$—CH$_2$)n-OH), 4.49 ppm (m, 4H, —CO—NH—CH—CH$_2$—C$_6$H$_5$), 4.57 ppm (m, 2H, —CO—NH—CH—CH$_2$—C$_6$H$_5$), 7.25 ppm (m, 10H, —CO—NH—CH—CH$_2$—C$_6$H$_5$), 7.74 ppm (m, 2H), 8.44 ppm (m, 2H), 8.61 ppm (m, 2H)

Example 5-31

Synthesis of Compound (p20)

(p20)

n = about 460

The compound (p19) (3.0 g) obtained in Example 5-2, sodium acetate (60 mg), and glutaric anhydride (86 mg) were dissolved in toluene (10 g), and the mixture was reacted under a nitrogen atmosphere at 40° C. for 6 hr. After completion of the reaction, the mixture was diluted with toluene (150 g), suction filtered using 5A filter paper, hexane (100 g) was added to the obtained filtrate, and the mixture was stirred at room temperature for 30 min. The resultant product was precipitated and suction filtered using 5A filter paper. The precipitate was recovered and the obtained precipitate was dissolved in toluene (200 g), hexane (100 g) was added, and the mixture was stirred at room temperature for 15 min. The resultant product was precipitated and suction filtered using 5A filter paper. The precipitate was recovered, washed with hexane (150 g) containing BHT (30 mg), suction filtered using 5A filter paper, and dried in vacuo to give the above-mentioned compound (p20). yield 2.3 g.

$^1$H-NMR ($d_6$-DMSO): 1.62 ppm (m, 4H, —CO—NH—CH$_2$—CH$_2$—CH$_2$—(O—CH$_2$—CH$_2$)n-OH), 1.97 ppm (m, 2H, —NH—CO—CH(NH$_2$)—CH$_2$—CH$_2$—), 2.02 ppm (m, 8H), 2.30 ppm (t, 2H, —CH$_2$—CH$_2$—CH$_2$—COOH), 2.74 ppm (dd, 2H, —CO—NH—CH—CH$_2$—C$_6$H$_5$), 2.81 ppm (dd, 2H, —CO—NH—CH—CH$_2$—C$_6$H$_5$), 3.64 ppm (m, about 3,800H, —CO—NH—CH$_2$—CH$_2$—CH$_2$—(O—CH$_2$—CH$_2$)n-OH), 4.57 ppm (m, 2H, —CO—NH—CH—CH$_2$—C$_6$H$_5$), 7.25 ppm (m, 10H, —CO—NH—CH—CH$_2$—C$_6$H$_5$), 7.74 ppm (m, 2H), 8.44 ppm (m, 3H), 8.61 ppm (m, 2H)

Example 5-4

Synthesis of Compound (p21)

(p21)

n = about 460

The compound (p18) (1.8 g) obtained in Example 5-1 and the compound (p20) (1.8 g) obtained in Example 5-3 were dissolved in acetonitrile. Thereafter, diisopropylethylamine (14 mg) and DMT-MM (373 mg) were added, and the mixture was reacted at room temperature under a nitrogen atmosphere for 3 hr. After completion of the reaction, the reaction mixture was diluted with toluene (200 g), hexane (100 g) was added, and the mixture was stirred at room temperature for 30 min. The resultant product was precipitated and suction filtered using 5A filter paper. The precipitate was recovered, dissolved in toluene (200 g) containing BHT (40 mg), hexane (100 g) was added, and the mixture was stirred at room temperature for 30 min. The resultant product was precipitated and suction filtered using 5A filter paper. The precipitate was recovered, washed with hexane (100 g) containing BHT (20 mg), suction filtered using 5A filter paper, and dried in vacuo to give the above-mentioned compound (p21). yield 2.4 g.

$^1$H-NMR (d$_6$-DMSO): 0.89 ppm (d, 6H, —NH—CO—CH—CH$_2$—CH(CH$_3$)$_2$), 0.91 ppm (d, 6H, —NH—CO—CH—CH$_2$—CH(CH$_3$)$_2$), 1.44 ppm (s, 18H, —CH$_2$—CH$_2$—CH$_2$—NH—CO—O—C(CH$_3$)$_3$), 1.48 ppm (m, 2H, —NH—CO—CH—CH$_2$—CH(CH$_3$)$_2$), 1.73 ppm (m, 16H), 2.05 ppm (m, 14H), 3.64 ppm (m, about 7,600H, —CO—NH—CH$_2$—CH$_2$—CH$_2$—(O—CH$_2$—CH$_2$)n-), 4.09 ppm (s, 12H), 4.44 ppm (m, 4H), 4.57 ppm (m, 4H, —CO—NH—CH—CH$_2$—C$_6$H$_5$), 6.76 ppm (broad, 2H), 7.25 ppm (m, 20H, —CO—NH—CH—CH$_2$—C$_6$H$_5$), 8.01 ppm (broad, 4H), 8.32 ppm (broad, 8H), 9.04 ppm (broad, 6H)

Example 5-5

Synthesis of Compound (p22)

(p22)

-continued n = about 460

The compound (p20) (2.0 g) obtained in Example 5-4 was dissolved in acetonitrile (20 g), p-nitrophenyl chloroformate (20 mg) and N-phenylmorpholine (20 mg) were added, and the mixture was reacted at room temperature under a nitrogen atmosphere for 3 hr. Thereafter, ion exchange water (7 mg) and N-phenylmorpholine (41 mg) were added, and the mixture was stirred. Aqueous 3-aminopropanoic acid solution (36 mg) and 10N aqueous sodium hydroxide solution (2.5 mL) were added, and the mixture was reacted at room temperature for 3 hr. After completion of the reaction, toluene (100 g) was added, and the mixture was concentrated and azeotropically dehydrated. Thereafter, the concentrate was diluted with toluene (30 g), suction filtered using 5A filter paper, hexane (30 g) was added to the filtrate and the mixture was stirred at room temperature for 30 min. The resultant product was precipitated and suction filtered using 5A filter paper. The precipitate was recovered, dissolved again in toluene (50 g) containing BHT (10 mg), hexane (30 g) was added, and the mixture was stirred at room temperature for 30 min and suction filtered using 5A filter paper. The precipitate was recovered, washed with hexane (30 g) containing BHT (6 mg), suction filtered using 5A filter paper, and dried in vacuo to give the above-mentioned compound (p22). yield 1.3 g.

$^1$H-NMR (d$_6$-DMSO): 0.89 ppm (d, 6H, —NH—CO—CH—CH$_2$—CH(CH$_3$)$_2$), 0.91 ppm (d, 6H, —NH—CO—CH—CH$_2$—CH(CH$_3$)$_2$), 1.44 ppm (s, 18H, —CH$_2$—CH$_2$—CH$_2$—NH—CO—O—C(CH$_3$)$_3$), 1.48 ppm (m, 2H, —NH—CO—CH—CH$_2$—CH(CH$_3$)$_2$), 1.73 ppm (m, 16H), 2.05 ppm (m, 14H), 2.49 ppm (t, 4H, —CO—NH—CH$_2$—CH$_2$—COOH) 3.64 ppm (m, about 7,600H, —CO—NH—CH$_2$—CH$_2$—CH$_2$—O—(CH$_2$—CH$_2$—O)n-), 4.09 ppm (s, 12H), 4.44 ppm (m, 4H), 4.57 ppm (m, 4H, —CO—NH—CH—CH$_2$—C$_6$H$_5$), 6.76 ppm (broad, 2H), 7.25 ppm (m, 20H, —CO—NH—CH—CH$_2$—C$_6$H$_5$), 8.01 ppm (broad, 4H), 8.32 ppm (broad, 8H), 9.04 ppm (broad, 6H)

Example 5-6

Synthesis of Compound (p23)

(p23)

-continued n = about 460

The compound (p22) (1.0 g) obtained in Example 5-5 was dissolved in ion exchange water (4.5 g), 6N hydrochloric acid (0.46 g) was added, and the mixture was reacted at room temperature under a nitrogen atmosphere for 3 hr. After completion of the reaction, 1N aqueous sodium hydroxide solution was added to adjust to pH 6.5, and sodium chloride (1.0 g) was added to the mixture and dissolved therein. To the obtained solution was added 1N aqueous sodium hydroxide solution to adjust to pH 7.10, chloroform (30 g) containing BHT (6 mg) was added, and the mixture was stirred at room temperature for 20 min and the resultant product was extracted into the organic layer. The organic layer and the aqueous layer were separated, the organic layer was recovered, chloroform (30 g) containing BHT (6 mg) was added again to the aqueous layer, and the mixture was stirred at room temperature for 20 min. The resultant product was extracted into the organic layer. The organic layers obtained by the first extraction and the second extraction were combined and concentrated at 40° C., the obtained concentrate was dissolved in toluene (100 g), hexane (50 g) was added, and the mixture was stirred at room temperature for 15 min. The resultant product was precipitated and suction filtered using 5A filter paper. The precipitate was recovered, washed with hexane (50 g) containing BHT (10 mg), suction filtered using 5A filter paper, and dried in vacuo to give the above-mentioned compound (p23). yield 532 mg. HPLC: The amine purity was 84%.

$^1$H-NMR ($d_6$-DMSO): 0.89 ppm (d, 6H, —NH—CO—CH—CH$_2$—CH(CH$_3$)$_2$), 0.91 ppm (d, 6H, —NH—CO—CH—CH$_2$—CH(CH$_3$)$_2$), 1.48 ppm (m, 2H, —NH—CO—CH—CH$_2$—CH(CH$_3$)$_2$), 1.73 ppm (m, 16H), 2.05 ppm (m, 14H), 2.49 ppm (t, 4H, —CO—NH—CH$_2$—CH$_2$—COOH), 2.68 ppm (t, 4H, —CH$_2$—CH$_2$—CH$_2$—NH$_2$), 3.64 ppm (m, about 7,600H, —CO—NH—CH$_2$—CH$_2$—CH$_2$—O—(CH$_2$—CH$_2$—O)n-), 4.09 ppm (s, 12H), 4.44 ppm (m, 4H), 4.57 ppm (m, 4H, —CO—NH—CH—CH$_2$—C$_6$H$_5$), 6.76 ppm (broad, 2H), 7.25 ppm (m, 20H, —CO—NH—CH—CH$_2$—C$_6$H$_5$), 8.01 ppm (broad, 4H), 8.32 ppm (broad, 8H), 9.04 ppm (broad, 6H)

TABLE 1

| sample name | | molecular weight (Mn) |
| --- | --- | --- |
| Example 1-2 | compound (p2) | 41,668 |
| Example 1-3 | compound (p3) | 41,711 |
| Example 2 | compound (p8) | 41,692 |
| Example 3 | compound (p13) | 41,325 |
| Example 4-3 | compound (p16) | 38,234 |
| Example 4-4 | compound (p17) | 38,145 |
| Example 5 | compound (p23) | 76,654 |

Example 6

Stability Test in Serum

Mouse or human serum (1 mL) was added to a 1.5 mL Eppendorf tube, and various polyethylene glycol derivatives were added to a concentration of 5.0 mg/mL. After incubation at 37° C. for 96 hr, 200 µL was sampled. Acetonitrile was added thereto, and the mixture was stirred by vortex for 1 min to precipitate the protein in serum. After centrifugation, the supernatant was collected. Then, to remove hydrophobic substances such as fatty acid and the like, hexane was added to the collected liquid, and the mixture was stirred by vortex for 1 min, centrifuged, and the lower layer was collected. This solution was concentrated under vacuum conditions and the polyethylene glycol derivative was recovered from the serum. Then, GPC analysis was performed and the degradation rate of the degradable polyethylene glycol derivative was calculated.

The degradation rate was calculated by the following formula.

degradation rate=(peak area % of main fraction before test−peak area % of main fraction after test)÷(peak area % of main fraction before test×100

The results are shown in the following Table 2.

TABLE 2

| sample name | | degradation rate in mouse serum | degradation rate in human serum |
|---|---|---|---|
| Example 1-2 | compound (p2) | 1% | 1% |
| Example 4-3 | compound (p16) | 0% | 1% |
| non-degradable | methoxy PEG 40 ka | 0% | 0% |

According to Table 2, the compounds (p2), (p16) which are degradable polyethylene glycol derivatives were not degraded in the serum, similar to methoxy PEG 40 kDa which is a non-degradable polyethylene glycol derivative. That is, it was shown that the degradable polyethylene glycol derivative is stable in blood.

Example 7

Degradability Test Using Cells

Using medium RPMI-1640 (10% FBS Pn/St) (10 mL), RAW264.7 was seeded at 10×10⁶ cells in a 100 mm dish, and cultured at 37° C. for 24 hr. The medium was exchanged with a medium in which various polyethylene glycol derivatives had been dissolved at a concentration of 10 mg/mL, and the cells were cultured at 37° C. for 96 hr. After culturing, the cells were lysed with 1% SDS solution, diluted with phosphate buffered saline (PBS), acetonitrile was added thereto, and the mixture was stirred for 1 min by vortex to precipitate the protein in the cell lysate, and after centrifugation, the supernatant was collected. Then, to remove hydrophobic substances such as fatty acids, hexane was added to the recovered liquid, and the mixture was stirred by vortex for 1 min, centrifuged, and the lower layer was recovered. This solution was concentrated under vacuum conditions to recover the polyethylene glycol derivative from the cells.

To confirm the degradation in the medium used for cell culture, media in which various polyethylene glycol derivatives had been dissolved at a concentration of 10 mg/mL were only cultured at 37° C. for 96 hr, and the polyethylene glycol derivative was recovered by the same operation as that described above.

Thereafter, the collected various polyethylene glycol derivatives were subjected to GPC analysis, and the degradation rate of the degradable polyethylene glycol derivative was calculated by the same calculation formula as in Example 7.

The results are shown in the following Table 3.

TABLE 3

| sample name | | degradation rate in medium | degradation rate in cell |
|---|---|---|---|
| Example 1-2 | compound (p2) | 1% | 99% |
| Example 4-3 | compound (p16) | 0% | 99% |
| non-degradable | methoxy PEG 40 ka | 0% | 0% |

According to Table 3, it could be confirmed that compounds (p2) and (p16) which are degradable polyethylene glycol derivatives are effectively degraded in the cells (degradation rate 99%), and degraded into a molecular weight of 40,000 to 20,000 in (p2) and a molecular weight of 40,000 to 10,000 in (p16). These degradable polyethylene glycol derivatives are not degraded in the medium used for cell culture. Thus, it was confirmed that they were specifically degraded in the cells. On the other hand, methoxy PEG amine 40 kDa which is a non-degradable polyethylene glycol derivative was not degraded in the cells.

Example 8

PEGylation of Salmon Calcitonin (sCT)

To salmon calcitonin (sCT) with the amino acid sequence: CSNLSTCVLG KLSQELHKLQ TYPRTNTGSG TP (SEQ ID NO: 1) (0.5 mg, $1.5 \times 10^{-7}$ mol, manufactured by PH Japan Co., Ltd.) was added 100 mM sodium borate buffer (pH 9.0) to adjust the sCT concentration to 2.0 mg/mL. The compound (p3) (0.6 mg, $1.5 \times 10^{-8}$ mol) obtained in Example 1 was added and the mixture was reacted at 4° C. for 24 hr. Thereafter, the reaction solution was dialyzed against 10 mM sodium acetate buffer (pH 5.0), and purified by ion exchange chromatography using HiTrap SP HP (5 mL, manufactured by GE Healthcare) to give PEGylated sCT. The molar yield was 39%.

RP-HPLC Analysis
    apparatus: "ALLIANCE" manufactured by WATERS
    detector: UV (280 nm)
    column: Inertsil WP300 C18 (GL Science)
    mobile phase A: 0.05% TFA-H$_2$O
    mobile phase B: 0.05% TFA-ACN
    gradient: changed to the order of B30% (0 min), B40% (5 min), B50% (15 min), B100% (16 min), B100% (20 min)
    flow rate: 1.0 mL/min
    column temperature: 40° C.

The purity of PEGylated sCT was calculated under the above-mentioned RP-HPLC analysis conditions.
RPLC Purity of PEGylated sCT: 98%
MALDI-TOF-MS Analysis
    apparatus: "autoflex3" manufactured by Bruker
    sample: 0.5 mg/mL, PBS solution
    matrix: saturated α-cyano-4-hydroxycinnamic acid (CHCA) solution (0.01% TFA-H$_2$O:ACN=2:1)

The sample (1 μL) and matrix (19 μL) were mixed and 1 μL was spotted on the target.

The molecular weight of the PEGylated sCT was measured under the above-mentioned MALDI-TOF-MS analysis conditions. molecular weight of PEGylated sCT: 48,585

Since compound (p3), which is a multi-arm polyethylene glycol derivative, has two active carbonate groups, it can bind two molecules of sCT. It could be confirmed that the molecular weight of PEGylated sCT increased by about the molecular weight of two molecules of sCT compared to the molecular weight of the starting material, compound (p3).
SDS-PAGE Analysis
    kit: NuPAGE (registered trade mark) Bis-Tris Precast Gel (gel concentration 4-12%) manufactured by Thermo Fisher Scientific
    staining solution: Coomassie brilliant blue solution (CBB solution) or iodine staining solution (BaCl$_2$+I$_2$ solution)

The PEGylated sCT was evaluated according to the recommended measurement conditions of the above-mentioned SDS-PAGE kit. In PEGylated sCT, a band was observed by CBB staining that selectively stains proteins and peptides, and a band was also observed by iodine staining that stains polyethylene glycol. Bands were seen in both stains, thus confirming that compound (p3), which is the polyethylene glycol derivative, was bonded to sCT.

INDUSTRIAL APPLICABILITY

The degradable polyethylene glycol derivative of the present invention is a high-molecular-weight polyethylene glycol derivative that does not cause vacuolation of cells, can be effectively used for modifying bio-related substances, is stable in the blood of living organisms, and is degraded in cells.

This application is based on patent application No. 2019-176230 filed in Japan, the contents of which are encompassed in full herein.

The invention claimed is:

1. A degradable polyethylene glycol derivative represented by the following formula (1):

$$[-X^1-L^1-(CH_2CH_2O)_{n1}L^3]_{a1}W^1-L^5-Q-L^6-W^2-[L^4-(OCH_2CH_2)_{n2}L^2-X^2]_{a2} \quad \text{formula (1)}$$

wherein n1 and n2 are each independently 45-950, $W^1$ and $W^2$ are each independently an oligopeptide of 2-47 residues, a1 and a2 are each independently 1-8, Q is a hydrocarbon chain having 2-12 carbon atoms and optionally containing an oxygen atom and/or a nitrogen atom, $X^1$ and $X^2$ are each independently a functional group capable of reacting with a bio-related substance, and $L^1$, $L^2$, $L^3$, $L^4$, $L^5$ and $L^6$ are each independently a divalent spacer.

2. The degradable polyethylene glycol derivative according to claim 1, wherein the oligopeptide for $W^1$ and $W^2$ is an oligopeptide having glycine as a C-terminal amino acid.

3. The degradable polyethylene glycol derivative according to claim 1, wherein the oligopeptide for $W^1$ and $W^2$ is an oligopeptide having at least one hydrophobic neutral amino acid having a hydropathy index of not less than 2.5.

4. The degradable polyethylene glycol derivative according to claim 1, wherein the total molecular weight is not less than 20,000.

5. The degradable polyethylene glycol derivative according to claim 1, wherein $X^1$ and $X^2$ are each independently selected from the group consisting of an active ester group, an active carbonate group, an aldehyde group, an isocyanate group, an isothiocyanate group, an epoxide group, a maleimide group, a vinylsulfonyl group, an acrylic group, a sulfonyloxy group, a carboxyl group, a thiol group, a dithiopyridyl group, an α-haloacetyl group, an alkynyl group, an allyl group, a vinyl group, an amino group, an oxyamino group, a hydrazide group, and an azide group.

6. A degradable polyethylene glycol derivative represented by the following formula (2):

$$X^1-L^1-(CH_2CH_2O)_{n3}L^3-W^3-L^5-Q-L^6-W^4-L^4-(OCH_2CH_2)_{n4}L^2-X^2 \quad \text{formula (2)}$$

wherein n3 and n4 are each independently 110-950, $W^3$ and $W^4$ are each independently an oligopeptide of 2-5 residues, Q is a hydrocarbon chain having 2-12 carbon atoms and optionally containing an oxygen atom and/or a nitrogen atom, $X^1$ and $X^2$ are each independently a functional group capable of reacting with a bio-related substance, and $L^1$, $L^2$, $L^3$, $L^4$, $L^5$ and $L^6$ are each independently a divalent spacer.

7. The degradable polyethylene glycol derivative according to claim 6, wherein the oligopeptide for $W^3$ and $W^4$ is an oligopeptide composed only of a neutral amino acid and having glycine as a C-terminal amino acid.

8. The degradable polyethylene glycol derivative according to claim 6, wherein the oligopeptide for $W^3$ and $W^4$ is an oligopeptide having at least one hydrophobic neutral amino acid having a hydropathy index of not less than 2.5.

9. A degradable polyethylene glycol derivative represented by the following formula (3):

$$[-X^1-L^1-(CH_2CH_2O)_{n1}L^3]_{b1}W^5-L^5-Q-L^6-W^6+L^4-(OCH_2CH_2)_{n2}L^2-X^2]_{b2}$$

formula (3)

wherein n1 and n2 are each independently 45-950, $W^5$ and We are each independently an oligopeptide consisting of 5 to 47 residues and having a symmetrical structure centered on glutamic acid, b1 and b2 are each independently 2-8, Q is a hydrocarbon chain having 2-12 carbon atoms and optionally containing an oxygen atom and/or a nitrogen atom, $X^1$ and $X^2$ are each independently a functional group capable of reacting with a bio-related substance, and $L^1$, $L^2$, $L^3$, $L^4$, $L^5$ and $L^6$ are each independently a divalent spacer.

10. The degradable polyethylene glycol derivative according to claim 9, wherein the oligopeptide with a symmetrical structure centered on glutamic acid for $W^5$ and $W^6$ is an oligopeptide having a structure of the following v1 or v2 or v3:

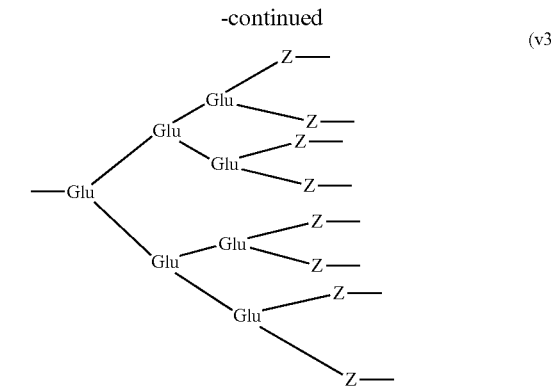

wherein Glu is a glutamic acid residue, and Z is a degradable oligopeptide of 2-5 residues consisting of neutral amino acids excluding cysteine.

11. The degradable polyethylene glycol derivative according to claim 10, wherein the degradable oligopeptide for Z is an oligopeptide having glycine as a C-terminal amino acid.

12. The degradable polyethylene glycol derivative according to claim 10, wherein the degradable oligopeptide for Z is an oligopeptide having at least one hydrophobic neutral amino acid having a hydropathy index of not less than 2.5.

13. A degradable polyethylene glycol derivative-bonded bio-related substance represented by the following formula (4):

$$[D^1-L^{11}-(CH_2CH_2O)_{n1}L^3]_{a1}W^1-L^5-Q-L^6-W^2+L^4-(OCH_2CH_2)_{n2}L^{12}-D^2]_{a2}$$

formula (4)

wherein n1 and n2 are each independently 45-950, $W^1$ and $W^2$ are each independently an oligopeptide of 2-47 residues, a1 and a2 are each independently 1-8, Q is a hydrocarbon chain having 2-12 carbon atoms and optionally containing an oxygen atom or a nitrogen atom, $D^1$ and $D^2$ are each independently a bio-related substance, and $L^3$, $L^4$, $L^5$, $L^6$, $L^{11}$ and $L^{12}$ are each independently a divalent spacer.

14. The bio-related substance according to claim 13, wherein $L^{11}$ and $L^{12}$ are each independently a urethane bond, an amide bond, an ether bond, a thioether bond, a secondary amino group, a carbonyl group, a urea bond, a triazolyl group, a bond of maleimide and mercapto, an oxime bond, or an alkylene group optionally comprising such bond and group.

15. The bio-related substance according to claim 13, wherein the bio-related substance for D is a hormone, a cytokine, an antibody, an aptamer or an enzyme.

* * * * *

SEQUENCE LISTING

```
<160> NUMBER OF SEQ ID NOS: 1

<210> SEQ ID NO 1
<211> LENGTH: 32
<212> TYPE: PRT
<213> ORGANISM: Salmo salar

<400> SEQUENCE: 1

Cys Ser Asn Leu Ser Thr Cys Val Leu Gly Lys Leu Ser Gln Glu Leu
1               5                   10                  15

His Lys Leu Gln Thr Tyr Pro Arg Thr Asn Thr Gly Ser Gly Thr Pro
            20                  25                  30
```